(12) United States Patent
Susulic et al.

(10) Patent No.: US 6,753,140 B2
(45) Date of Patent: Jun. 22, 2004

(54) TRANSCRIPTIONAL REGULATION OF THE HUMAN $\beta_3$-ADRENERGIC RECEPTOR GENE

(75) Inventors: Vedrana S. Susulic, Princeton Junction, NJ (US); Emir Duzic, Nanuet, NY (US)

(73) Assignee: Wyeth, Madison, NJ (US)

( * ) Notice: Subject to any disclaimer, the term of this patent is extended or adjusted under 35 U.S.C. 154(b) by 10 days.

(21) Appl. No.: 09/761,116

(22) Filed: Jan. 16, 2001

(65) Prior Publication Data

US 2002/0102552 A1 Aug. 1, 2002

Related U.S. Application Data

(62) Division of application No. 09/243,335, filed on Feb. 1, 1999, now Pat. No. 6,197,580.

(51) Int. Cl.[7] .......................... C12Q 1/68; C12N 15/00; C12N 15/09; C12N 15/86; C07H 21/04
(52) U.S. Cl. .......................... 435/6; 435/69.1; 435/29; 435/455; 536/23.1
(58) Field of Search .............................. 435/6, 29, 325, 435/69.1, 455; 536/23.1

(56) References Cited

U.S. PATENT DOCUMENTS

| 5,364,772 A | * 11/1994 | Granneman et al. ....... 435/69.1 |
| 5,683,912 A | 11/1997 | Elgoyhen et al. |
| 5,789,654 A | 8/1998 | Lowell et al. |

FOREIGN PATENT DOCUMENTS

WO    WO 94/02590    2/1994

OTHER PUBLICATIONS

Moriko Ito et al, Mice Expressing Human But Not Murine B3–Adrenergic Receptors Under the Control of Human Gene Regulatory Elements, Diabetes, vol. 47, Sep. 1998.*
Ito et al (1998) Mice expressing human but not murine beta3–adrenergic receptors under the control of human gene regulatory elements. Diabetes 47:1464–1471.
Wilson et al (1995) *C. elegans* cosmic F18E9. GenBank accession No. U29614, Jun. 22, 1995, accessed, Jan. 15, 2000.
Ohara, et al. "*Homo sapiens* mRNA for KIAA0537" EMHUM Database Entry AB01109, Accession No. AB011109.
Razik et al., J. Biol. Chem., 272:28237–28246, 1997.
Cohen, et al., The American Society for Biochemistry and Molecular Biology, Inc. 272:2901–2913, 1997.
Viñals, et al., The Journal of Biological Chemistry 272:12913–12921, 1997.
McPherson et al., PNAS 94:4342–4347, 1997.
Strosberg, Ann. Rev. Pharmacol. Toxicol. 37:421–450, 1997.

Yoshioka et al., Diabetologia 39: 1410–1411, 1996.
Fujisawa et al., Diabetologia 39:349–352, 1996.
Zhang et al., Diabetologia 39:1505–1511, 1996.
Wilson et al., The Journal of Pharmacology and Experimental Therapeutics 279:214–221, 1996.
Champigney and Ricquier, J. of Lipid Res., 37:1907–1914, 1996.
Rolland et al., The Journal of Biological Chemistry 271:21297–21302, 1996.
Granneman and Lahners, Endocrinology 135, 1025–1035, 1994.
Largis et al., Drug Dev. Res. 32:69–76, 1994.
Lönnqvist et al. Br. J. Biochem., 110: 929–936, 1993.
Krief et al., J. Clin. Invest. 91:344–349, 1993.
Van Spronsen et al., Eur. J. Biochem. 273:1117–1124, 1993.
Thomas et al., Mol. Pharmacol., 43:343–348, 1993.
Liggett, et al., Mol. Pharmacol., 42:634–637, 1992.
Granneman et al., Mol. Pharmacol. 42:964–970, 1992.
Yamamoto et al., Transcriptional Regulation, Cold Spring Harbor Laboratory Press, 1992, pp. 1169–1192.
Nahmias, et al., EMBOJ., 10:3721–3727, 1991.
Liggett et al., J. DNA Sequencing and Mapping 2:61–63, 1991.
Thomas and Liggett, Mol. Pharmacol., 43:343–343, 1991.
Muzzin et al., J. Biol Chem. 266:24053–24058, 1991.
Emorine et al., Science 245:1118–1121, 1989.
Dawson et al., The Journal of Biological Chemistry 263:3372–3379, 1988.
Kobilka et al., The Journal of Biological Chemistry 262:7321–7327, 1987.
Cantor et al., Nucl. Acids Res. 12:8059–8072, 1984.

\* cited by examiner

*Primary Examiner*—Gerry Leffers
(74) *Attorney, Agent, or Firm*—Darby & Darby

(57) ABSTRACT

Regulatory elements responsible for tissue-specific transcriptional regulation of the human $\beta_3$-adrenergic receptor ($\beta_3$-AR) were identified. A region localized between –6.50 and –6.30 kb of the proximal promoter contained three sequences that act synergistically to achieve full transcriptional activity. One segment, termed segment A, contains an Sp1 binding site. Another of the sequences, termed segment B, is a binding site for a trans-acting factor present in cells that constitutively express $\beta_3$-AR. In a specific embodiment, the trans-acting factor is expressed in neuroblastoma (SK-N-MC) and brown adipose tissue cells, but little or not at all in CV-1, HeLa, or white adipose tissue cells. The third segment, C, is an S1 nuclease-sensitive site having CCTT repeats. Recombinant vectors under control of this transcriptional regulation region, particularly containing the B and C segments, provide a substrate for high throughput assays, such as reporter gene assays, to identify compounds that can increase the level of expression of $\beta_3$-AR. The B segment nucleic acids also provide for isolation and cloning of the trans-acting factor. Mechanisms of transcriptional regulation and identification of other adjacent proteins involved in the regulation of the h$\beta_3$-AR gene expression are provided.

12 Claims, 9 Drawing Sheets

FIG. 2 tcccattggc catcctccccc actctccaat tcggctccag aggccccctcc agactatagg cagctgcccc tttaagcgtc
\*                                                        \*                                \* gctactcctc cccaagagc ggtggcaccg agggagttgg ggtggggggga ggctgagcgc tctggctggg acagctagag
                        \* aagatggccc aggctgggga gtcgctctca tgccttgctg tcccctcccct gagccaggtg atttgggaga ccccctcctt ccttcttttcc ctaccgcccc acgcgcgacc cggggATGg ctccgtggcc tcacgagaac agctctcttg ccccatggcc ggacctcccc accctgggcgc ccaataccgc caacacctgg gctgccagggg ttccgtgggga ggcggca

CCTGGAAGGAAGCCTAAGCATTTGGGCCTGGGTGTAGGTGGACTCGTGACCTCTCCC
_____1_____  _____2_____
                                          ━━━━━━━━━━━2A━━━━━━━━━

AGCCTCTGGGAGCAGCTTCTCCAATAGTCAGGGTCAATGACCTTCCTTCCTTCCTT
━━━━━━━━━2━━━━━━━━━  _____3_____
                     _____3A_____          ∙∙∙∙∙∙∙4A∙∙∙∙∙∙∙

CCTTCCTTCCTTCCTTCCTTCCTTCCTTCCTTCCTTCCTTCCTTCCTTCCTTCTC
∙∙∙∙∙∙4A∙∙∙∙∙∙        _____4_____  – – 1A – –
                                                    – – – – – 1B – – – – –

CTTCCTTCCTTCGTGCCACTTGCAAAAG
– – – 1A – – –

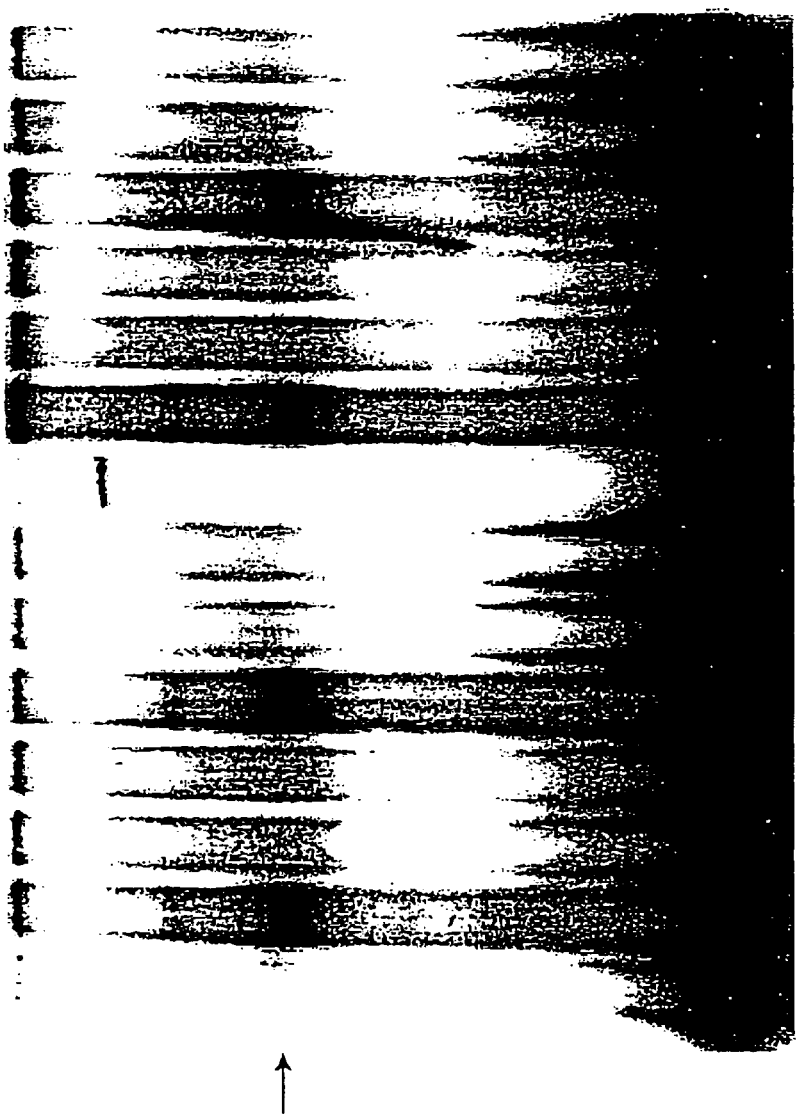

FIG. 7

Segment A
(overlap between oligo 1 and 2)

A1 gatccGGTTGTAGGTGGGACTCGTGAa
A2 gatccCTATGTAGGTGGGACTCGTGAa
A3 gatccGGTACAAGGTGGGACTCGTGAa
A4 gatccGGTTGTTCCTGGGACTCGTGAa
A5 gatccGGTTGTAGGACCGACTCGTGAa
A6 gatccGGTTGTAGGTGGCTGTCGTGAa
A7 gatccGGTTGTAGGTGGGACAGCTGAa
A8 gatccGGTTGTAGGTGGGACTCGACTa

Segment B
(overlap between oligo 2 and 3A)

B1 gatccGCCTCTGGGGAGCAGCTTCTCCa
B2 gatccCGGTCTGGGGAGCAGCTTCTCCa
B3 gatccGCCAGAGGGGAGCAGCTTCTCCa
B4 gatccGCCTCTCCCGAGCAGCTTCTCCa
B5 gatccGCCTCTGGGCTCCAGCTTCTCCa
B6 gatccGCCTCTGGGGAGGTCTTCTCCa
B7 gatccGCCTCTGGGGAGCAGGAACTCCa
B8 gatccGCCTCTGGGGAGCAGCTTGAGGa

TRANSCRIPTIONAL REGULATION OF THE HUMAN $\beta_3$-ADRENERGIC RECEPTOR GENE

This application is a division of application Ser. No. 09/243,335, filed Feb. 1, 1999, now U.S. Pat. No. 6,197,580, which is herein incorporated by reference in its entirety.

FIELD OF THE INVENTION

The present invention relates to a positive cis-regulatory (enhancer) element of human $\beta_3$-adrenergic receptor responsible for its transcription in SK-N-MC cells. Such element is composed of three DNA binding sites that act synergistically and is located 6.5 kb upstream from the translation start site of the $\beta_3$-adrenergic receptor. The invention further relates to use of this enhancer element for regulated gene expression and for drug screening.

BACKGROUND OF THE INVENTION

The $\beta_3$-adrenergic receptor ($\beta_3$-AR) is an important regulator of metabolic activity in brown and white adipose tissue, two major sites for regulation of energy balance. The $\beta_3$-AR belongs to a family of G-protein coupled receptors. Its binding to endogenous ligand or specific synthetic agonist leads to activation of adenylate cyclase, an increased concentration of cAMP, and an increased activity of PKA, resulting in increased thernogenic activity and heat production in brown adipose tissue (BAT) and lipolysis in white adipose tissue (WAT). Since $\beta_3$-AR stimulation causes an increase in thermogenic activity and a less efficient utilization of metabolic fuels, its sustained activation should be of benefit in the treatment of obesity, and improvement of glycemic control in type II diabetes. Indeed, numerous reports have shown that stimulation of $\beta_3$-ARs cause weight loss and improvement in glycemic control in rodent models of these diseases (Carroll et al., Diabetes 34:1198–1204, 1984; Umekawa et al., European Journal of Endo.136:429–437, 1997; Yoshida et al, J. Nutr. Sci. Vitaminol (Tokyo) 36:75–80, 1990; Yoshida et al., Endocrinol Japon 38:397–403, 1991; Smith et al., New Antidiabetic Drugs, Ed.: Bailey, C. J., and Flatt, P. R., London, 1990; Largis et al., Drug Dev. Res. 32:69–76, 1994; Bloom et al., Journal of Medicinal Chemistry 35:3081–3084, 1992; Cawthorne et al., American Journal of Clinical Nutrition 55:252S–257S, 1992).

Despite the well characterized role of $\beta_3$-ARs in rodents, its role in the regulation of energy balance in man is still not clear. Observations by several groups of investigators (Walston et al., New Engl. J. Med. 333:343–347, 1995; Kadowaki et al., Biochem. Biophys. Res. Commun. 215:555–560, 1995; Yoshioka et al., Diabetologia 39: 1410–1411, 1996; Fujisawa et al., Diabetologia 39:349–352, 1996; Kurabayashi et al., Diabetes 45:1358–1363, 1996; Zhang et al., Diabetologia 39:1505–1511, 1996; Widen et al., New Engl. J. Med. 333:348–351, 1995; Clement etal., New Engl. J. Med. 333:352–354, 1995) describing the existence of a positive correlation between an Arg to Trp mutation at position 64 in the human $\beta_3$-AR (h$\beta_3$-AR) gene and the early onset of non-insulin dependent diabetes mellitus (NIDDM) (Walston et al, supra; Yoshioka et al., supra; Fujisawa et al., supra; Kurabayashi et al., supra; Widen et al., supra), insulin resistance (Walston et al., supra), increased weight gain (Kadowaki et al., supra; Yoshioka et al. supra; Fujisawa et al. supra; Zhang et al, supra; Clement et al., supra) and abdominal obesity (Walston et al., supra) seemed to validate the role of the $\beta_3$-AR in the development of obesity and diabetes. However, other investigators have failed to observe any correlation between the prevalences of the Tr$\beta_{64}$Arg mutation and obesity or diabetes in the patient populations they have studied (Li, et al., Diabetologia 39:857–860, 1996; Elbein et al., J. Clin. Endocrinol. Metab. 81:4422–4427, 1996; Ueda et al., Metabolism 46:199–202, 1997; Awata et al. Diabetes Care 19:271–272, 1996). Further, the pharmacology and biology of the wild type and mutated receptors did not differ when compared in cell based systems (Candelore et al., Endocrinology 137:2638–2641, 1996; Pietri-Rouxel et al., Eur. J. Biochem. 247:1174–11791 1997), although it does appear that the mutations cause less accumulation of cAMP, indicating diminished signal transduction efficiency in the cells that contained mutated h$\beta_3$-AR. The physiological significance of this observation is not yet clear. The success achieved in the treatment of obesity and diabetes in rodent models with selective $\beta$3-AR agonists supported a role for this receptor as a therapeutic target and has prompted a great effort to develop compounds with a high affinity and selectivity towards the human $\beta$3-AR.

Despite the approximately 80% homology in amino acid sequences and similar adipose tissue expression pattern, human and mouse $\beta_3$-ARs differ in two very important ways. First, the mouse $\beta$3-AR shows a high affinity and selectivity for certain $\beta_3$-AR specific agonists, while the human receptor has little or no affinity for the same agonists when tested in CHO cells stably transfected with human $\beta_3$AR (Liggett et al., Molecular Pharmacology, 42:634–637, 1992). On the other hand, agonists that show high affinity and selectivity in $\beta_3$-AR transfected CHO cells that express a high level of human $\beta_3$-ARs have little or no activity in vivo (when tested in non human primates and clinical trials). Their lack of robust activity may be due to pharmacokinetic or metabolic issues, but another reason for this discrepancy may be the low level of $\beta_3$-AR expression in target tissues (Wilson et al., The Journal of Pharmacology and Experimental Therapeutics 279:214–221, 1996).

Second, in rodents $\beta_3$-AR mRNA is predominantly detected in brown and white adipose tissue (Granneman et al., Mol. Pharmacol. 40:895–899, 1991; Muzzin et al., J. Biol Chem. 266:24053–24058, 1991), while in man $\beta_3$-ARs are expressed in BAT but appear to have little or no expression in WAT (Krief et al., J. Clin. Invest. 91:344–349, 1993; Thomas and Liggett, Mol. Pharmacol., 43:343–343, 1991). However, other studies support the existence of functionally active $\beta_3$-ARs in human WAT, showing an increase in lipolysis and glycerol formation after treatment with CGP-1 2177 (a selective agonist for the human $\beta_3$-AR) both in vivo (Lonnqvist, Br. J. Pharmacol., 1993) and in vitro (Enocksson et al., J. Clin. Invest. 95:2239–2245, 1995). The significance of these studies in terms of the importance of $\beta_3$-ARs in the regulation of WAT physiology remains to be proven, since CGP-12177 might interact with other as yet undescribed adrenergic receptors (Kaumann, A. J., Trends in Pharmacological Sciences 18:70–76, 1997).

The low affinity for synthetic agonists together with a low level of expression of h$\beta_3$-ARs in WAT and the relatively small amount of BAT in humans may explain why agonists developed so far have been inactive in man.

Although the beneficial effects of an increased presence of $\beta_3$-ARs in man can be envisioned, research leading to a better understanding of the factors that regulate the h$\beta_3$-AR gene expression has been limited. Given the possibility that increased expression of $\beta_3$-AR in humans will lead to an increased accessibility of receptors in WAT and BAT, as well as to the recruitment of more brown adipocytes, there is a need in the art to better understand mechanisms and factors that regulate transcription of h$\beta_3$-ARs.

This problem is rendered more complex due to the lack of human brown and white adipose tissue cell lines. Although the genes for mouse (Nahmias et al., EMBO J. 10:3721–3727, 1991), rat (Granneman et al., Mol. Pharmacol. 40:895–899, 1991), and human $\beta_3$-ARs (Granneman et al., Mol. Pharmacol. 44:264–270, 1993); Granneman et al., Mol. Pharmacol. 42:964–970, 1992; Emorine et al., Science 245:1118–1121) have been cloned, little additional data is available about the structure of regulatory regions and possible transcription factors close to the proximal promoter that may play a role in $\beta_3$-AR transcriptional regulation (Liggett et al., J. DNA Sequencing and Mapping 2:61–63, 1991). Thus, there is a need in the art to provide the endogenous regulatory sequences of $\beta_3$-AR.

SUMMARY OF THE INVENTION

In one aspect, the present invention provides an isolated nucleic acid comprising a nucleotide sequence that is greater than 80% identical to the nucleotide sequence GCCTCTGGGGAG (SEQ ID NO: 1). This sequence is specifically recognized by a transcription factor, and is responsible for tissue specific expression of $\beta_3$-AR. The invention further provides this nucleic acid further comprising a nucleotide sequence that binds an Sp-1 transcription factor protein, or contains an S1 nuclease sensitive site, or both. A combination of these sequences in proximity to each other in a nucleic acid, termed herein a $\beta_3$-AR enhancer element, permits positive regulation of expression of a gene operably associated with the sequences. Host cells containing vectors, with genes operably associated with the enhancer element, and both transient and stable expression of such genes, are also provided.

The invention further provides a specific $\beta_3$-AR trans-activating factor polypeptide having the following characteristics: (a) it binds specifically to the nucleic acid having the sequence GCCTCTGGGGAG (SEQ ID NO: 1); (b) it is expressed by mouse brown adipose tissue cells; (c) it is expressed at very low levels by human white adipocytes isolated from the perirenal depot; (d) an AP-2 binding oligonucleotide does not compete with a nucleic acid having the nucleotide sequence GCCTCTGGGGAG (SEQ ID NO: 1) for binding the polypeptide; and (e) when complexed to a nucleic acid comprising SEQ ID NO: 1, it is not recognized by an antibody to AP-2, e.g., as detected in a super shift assay.

In another aspect, the invention provides a method of isolating a polypeptide that binds specifically to a nucleic acid having a nucleotide sequence GCCTCTGGGGAG (SEQ ID NO: 1). The method comprises contacting a composition suspected of containing the polypeptide with the nucleic acid under conditions that permit detection of binding of the polypeptide to the nucleic acid; and isolating the bound polypeptide.

In still another embodiment, the invention provides a method of screening for a compound that increases activity of a $\beta_3$-AR trans-activating factor in human cells. This method comprises contacting cells with a test compound; and detecting an increase in a level of activity of the $\beta_3$-AR trans-activating factor.

A related method of the invention provides for screening for a compound that inhibits activity of a $\beta_3$-AR trans-activating factor in human cells. Such a method comprises contacting cells with a test compound; and detecting a decrease in a level of activity of the $\beta_3$-AR trans-activating factor.

In both screening methods, the test cells are capable of producing, i.e., expressing, one or more components of the $\beta_3$-AR trans-activating factor.

These and other aspects of the present invention are further elaborated in the drawings and detailed description that follow.

BRIEF DESCRIPTION OF THE DRAWINGS

FIG. 2: Determination of transcription start site of h$\beta_3$-AR gene using 5' RACE. 5' RACE was performed on poly A RNA (SEQ ID No:49) isolated from SK-N-MC cells using the Marathon cDNA amplification kit (Clontech). Twenty subcloned RACE-PCR products were subcloned and sequenced. Capital letters in the Figure represent translation start sites. The underlined sequence represents the primer used in 5' RACE; determined transcription start sites are indicated with asterisks.

FIGS. 7A and 7B: Mutational analysis of regions "A" and "B". A: Segment "A" oligonucleotides (SEQ ID NOS: 33–40 representing the overlap between oligonucleotides 1 and 2. B: Segment "B" oligonucleotides (SEQ ID NOS: 41–48) representing the overlap between oligonucleotides 2 and 3A. Mutated oligonucleotides are shown, with mutated bases underlined. Small letters correspond to restriction enzymes sites for easier cloning and purification of doublestranded oligonucleotides.

DETAILED DESCRIPTION OF THE INVENTION

Figure 1:
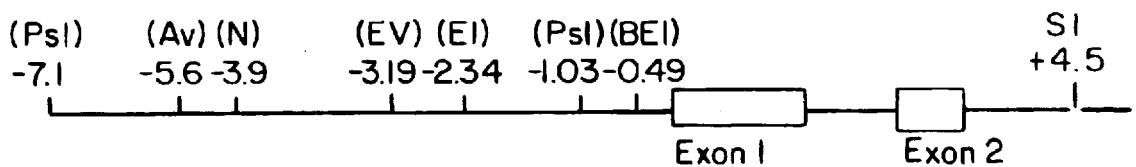
FIG. 1: Partial restriction enzymes map of 7A human $\beta_3$-AR clone. A human lung genomic library was screened with a probe that corresponds to the full cDNA region except the last 6 amino acids. The probe was made by ligation of 4 PCR products that overlap partial cDNA for the h$\beta_3$-AR gene. The map shows restriction enzymes sites and their corresponding position within the genomic DNA from the translation start site (PsI-Pst I, Avr-AvII, EV-EcoRV, El-EcoRI, BE-BstEII, SI-SalI).

The present invention is based, in part, on the discovery of a new regulatory region that appears to be an enhancer element for the human $\beta_3$-AR gene. Mechanisms of transcriptional regulation of the human $\beta_3$-adrenergic receptor were studied using SK-N-MC cells, a human neuroblastoma cell line that expresses $\beta_3$- and $\beta$1-adrenergic receptors endogenously. A genomic 7 kilobase (kb) region of the human $\beta_3$-adrenergic receptor 5' flanking region was isolated. Transfection constructs that contain deletions within this 7 kb region linked to a luciferase reporter gene were made and transfected in SK-N-MC, CV1 and HeLa cells. Maximal luciferase activity was observed only with the presence of a 200 basepair (bp) region located far upstream (between −6.5 kb and −6.3 kb) from the translation start site. This region was also shown to determine cell-specific expression in SK-N-MC cells, but not CV1 or HeLa cells. Electrophoretic mobility shifts assays using nuclear extracts from SK-N-MC, CV-1 and HeLa cells with oligonucleotides that cover this 200 bp promoter region revealed the existence of three cis-regulatory elements (segments A, B, and C), or protein binding segments, that act synergistically to achieve full transcriptional activity. Mutational analysis, along with antibody-supershift studies and competition experiments, implicated an Sp1 transcription factor as a part of the positive regulatory element (segment A). Segment B represents a novel DNA binding site that binds a protein present in nuclear extracts from SK-N-MC cells and brown adipose tissue, but which was not detectable in other cells, notably white adipose tissue by methods used in the Examples, infra. These data support the brown adipose tissue-specific expression of the $\beta_3$-adrenergic receptor. Segment C binds protein present in SK-N-MC and HeLa cells; it also exhibits an S1 nuclease hypersensitive site. These data taken together indicate the existence of cell specific positive cis-regulatory elements located 6.5 kb upstream from the translation start site that play a pivotal role in transcriptional regulation of the human $\beta_3$-adrenergic receptor.

The nucleotide sequence of a nucleic acid (DNA) that binds a tissue-specific trans-activating factor has been identified in segment B of the $\beta_3$-AR regulatory region. The sequence is greater than 80% identical (at least 10 of 12 bases are the same) to the core nucleotide sequence GCCTCTGGGGAG (SEQ ID NO: 1). In a specific embodiment, the sequence of this segment is GCCTCTGGGGAG (SEQ ID NO: 1). In another specific embodiment, the sequence is 78% similar to an ERF AP-2 consensus binding site. However, an oligonucleotide comprising the segment B core sequence cannot displace binding of an AP-2 oligonucleotide by an AP-2 protein, even at a 100-fold molar excess. Segment B can be further characterized by its specificity for binding with a trans-activating factor found at detectable levels in brown adipose tissue (BAT) and in a human neuroblastoma cell line, but which is not detectably present in HeLa cells, or in white adipose tissue (WAT) (murine, and probably human as well). Thus, in a specific embodiment, an isolated nucleic acid comprising a nucleotide sequence of the invention can be identified by its specificity for the particular trans-activating factor.

The new trans-activating factor is termed herein the "B segment-binding trans-activating factor." This B segment-binding trans-activating factor polypeptide appears to be an AP-2-like protein. This conclusion is based on the similarity of the B segment sequence, specifically SEQ ID NO: 1, to an ERF consensus binding site that belongs to a family of AP-2 transcription factors. In a specific embodiment, infra, the B segment-binding trans-activating factor binds a nucleic acid comprising the sequence GCCTCTGGGGAG (SEQ ID NO: 1) with high enough affinity that an AP-2 oligonucleotide competitor failed to displace it, even at a 200-fold molar excess. In a further embodiment, the B segment-binding trans-activating factor does not bind an antibody that recognizes AP-2.

A second protein-binding segment that operates synergistically with segment B in the regulatory region has also been identified. Because in a specific embodiment this segment is upstream (5') to segment B, it has been termed segment A. Segment A binds an Sp1-like transcription factor. In specific embodiments, segment A is displaced from binding a protein from cellular nuclear extracts by an Sp1 oligonucleotide. In another embodiment, a protein that binds to segment A is recognized by an anti-Sp1 antibody. Thus, in a specific embodiment, segment A is an Sp1 binding site. In a further specific embodiment, exemplified infra, the nucleotide sequence of the binding site is AGGTGGGACT (SEQ ID NO: 2). This binding site sequence differs from known Sp1 sequences. It contains a "GGTG" motif, whereas known Sp1 sequences have a "GGCG" motif.

A third protein-binding segment that is necessary for the positive regulatory effects of segment A and segment B, alone and in combination, has also been identified. Because in a specific embodiment exemplified infra this segment is 3' to segment B, it has been termed segment C. Segment C is an S1 nuclease-sensitive site. In a specific embodiment, it comprises at least 12 bases, and preferably about 80 bases, of a homopurine-homopyrimidine rich region. In a more specific embodiment, segment C comprises at least 3, and preferably about 20, repeats of the sequence CCTT. In a specific embodiment exemplified infra, there are 19 repeats of CCTT and one repeat, in the $19^{th}$ position, with the sequence TCTT (for a total of 20 repeats). Segment C is found to be essential for transcriptional activity of segments A and B.

The tissue-specific trans-activating factor binding sequence that has been termed herein segment B, along with the Sp1 transcription activation factor binding sequence termed herein segment A and the S1 nuclease-sensitive segment that is a protein binding site termed herein segment C (collectively, regulatory segments), can be combined to create a regulatory region that positively regulates gene expression in a tissue-specific manner. The regulatory region of the invention comprising all three segments has the attributes of an enhancer element, and the term "$\beta_3$-AR enhancer element" or "enhancer element" may be used herein for the regulatory region of the invention comprising all three segments. In a specific embodiment, the enhancer element is a 200 base-pair sequence as depicted in FIG. 6A (SEQ ID NO: 3).

As used herein, a "$\beta_3$-AR trans-activating factor" refers to a polypeptide or polypeptide complex that recognizes the enhancer element. This complex includes the AP-2 like B segment trans-activating factor polypeptide, Sp1, and the C segment-specific polypeptide. It also includes other binding factors that may interact with genomic DNA sequences present on the approximately 7 kb DNA upstream of the $\beta_3$-AR start site.

A nucleic acid vector, such as a plasmid, containing these sites, or combinations of A and C or B and C, in proximity to each other and upstream a distance of about 0 to about 10 kb from a promoter region operatively associated with a gene on an expression vector can increase the level of expression of the gene. Inclusion of the B segment confers tissue specificity: expression of the gene under control of the enhancer element only occurs in cells that have a transcription factor that binds to the core binding sequence of segment B. All three segments together (the enhancer element) synergistically increase expression levels of a gene operably associated with the enhancer element under appropriate expression conditions (i.e., when the B segment binding protein is present in the cell). The three segments can be oriented in either orientation in the 5' flanking region of a gene. Thus, in one embodiment, the segments are arranged in A-B-C order on the coding strand relative to the translation start site. In another embodiment, the segments are arranged in A-B-C order on the non-coding strand (and thus in [-C]-[-B]-[-A] order on the coding strand, where [-C] is the complement of the C segment, [-B] is the complement of the B segment, and [-A] is the complement of the A segment). Preferably, to ensure proper positioning to allow interaction between binding factors, and to reveal, to the extent possible, activation and binding domains after conformational changes, the three segments are arranged in A-B-C order, with the relative spacing between each segment found, e.g., in SEQ ID NO: 3.

As used herein, the term "proximity" when applied to the protein binding segments of the enhancer element means that the sites are located in a range from 1 to about 100 nucleotides from each other, and preferably, from about 10 to about 30 nucleotides from each other. In specific embodiments, segment A is located about 14 nucleotides upstream of segment B, and segment B is located about 31 nucleotides upstream of segment C.

In a specific embodiment, exemplified infra, the enhancer element is found in a nucleic acid (genomic DNA) isolated from a region about 7 kb upstream (−7 kb) of the $\beta_3$-adrenergic receptor ($\beta_3$-AR) transcription initiation (start) site. More specifically, the enhancer element can be located between −6.5 kb and −6.3 kb of the translation start site of the gene. In particular, a 200 bp region of the 5' flanking region of $\beta_3$-AR demonstrates the enhancer activity. In other embodiments, exemplified infra, location of the enhancer adjacent to 500 bp of the translation start site of the gene, and in locations between −7 kb and −0.5 kb, results in positive regulation of gene expression. The enhancer element operates with a heterologous promoter. In a specific embodiment, the enhancer element regulates gene expression from a herpes simplex virus (HSV) thymidine kinase (tk) minimal promoter. In another embodiment, the enhancer element operates more efficiently in conjunction with a $\beta_3$-AR promoter (found −0.5 kb from translation start site).

As used herein, the term "about" or "approximately" means within 20%, preferably within 10%, and more preferably within 5% of a given value or range.

As used herein, the term "isolated" means that the referenced material is free of components found in the natural environment in which the material is normally found. In particular, isolated biological material is free of cellular components. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate unrelated materials, i.e., contaminants. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Vector Constructs

The protein binding segments identified herein can be used in recombinant construction of expression vectors with positive regulation of gene expression. As noted above, the A and C or B and C segments can be used together to achieve positive regulation of gene expression. Furthermore, use of all three segments synergistically enhances gene expression. Accordingly, as used herein, use of a regulatory element of the present invention in a recombinant expression vector relates to any of the foregoing combinations, unless a specific combination is explicitly stated.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a recombinant nucleic acid construct, such as plasmid, phage genome, virus genome, cosmid, or artificial chromosome to which another DNA segment may be attached. In a specific embodiment, the vector may bring about the replication of the attached segment, e.g., in the case of a cloning vector. A "replicon" is any genetic element (e.g., plasmid, chromosome, virus) that functions as an autonomous unit of DNA replication in vivo, i.e., it is capable of replication under its own control.

A "cassette" refers to a segment of DNA that can be inserted into a vector at specific restriction sites. The segment of DNA that can be inserted encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when transfected DNA is expressed.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature. For example, a regulatory element of the invention is operatively associated with a heterologous gene when the gene is not a gene encoding human $\beta_3$-AR.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA:DNA, DNA:RNA and RNA:RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "gene" is used herein to refer to a portion of a DNA molecule that includes a polypeptide coding sequence operatively associated with expression control sequences. In one embodiment, a gene can be a genomic or partial genomic sequence, in that it contains one or more introns. In another embodiment, the term gene refers to a cDNA molecule (i.e., the coding sequence lacking any introns).

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

"Expression control sequences", e.g., transcriptional and translational control sequences, are regulatory sequences that flank a coding sequence, such as promoters, enhancers, suppressors, terminators, and the like, that provide for the expression of a coding sequence in a host cell. In eukaryotic cells, polyadenylation signals are control sequences. On mRNA, a ribosome binding site is an expression control sequence.

A coding sequence is "operatively associated with" or "under the control" of transcriptional and translational control sequences in a cell when RNA polymerase transcribes the coding sequence into mRNA, which is then trans-RNA spliced and translated into the protein encoded by the coding sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. In a specific embodiment, the $\beta_3$-AR promoter extends about 0.5 Kb 5' to the translation start site.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55° C., can be used, e.g., 5× SSC, 0.1% SDS, 0.25% milk, and no formamide; or 30% formamide, 5× SSC, 0.5% SDS. Moderate stringency hybridization conditions correspond to a higher $T_m$, e.g., 40% formamide, with 5× or 6× SSC. High stringency hybridization conditions correspond to the highest $T_m$, e.g., 50% formamide, 0.1× SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4× SSC, or under conditions that afford levels of hybridization equivalent to those observed under either of these two conditions.

As used herein, the term "oligonucleotide" refers to a nucleic acid, generally of at least 10, preferably at least about 15, and more preferably at least about 20 nucleotides, that is hybridizable to a genomic DNA molecule, a cDNA molecule, or an mRNA molecule encoding a regulatory or protein binding segment, a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the enhancer element, or to detect the presence of nucleic acids encoding the enhancer element. In a further embodiment, an oligonucleotide of the invention can form a triple helix with a DNA molecule containing one or more of the segments found in the enhancer element, e.g., to suppress positive regulation of the enhancer. Generally, oligonucleotides are prepared synthetically, preferably on a nucleic acid synthesizer. Accordingly, oligonucleotides can be prepared with non-naturally occurring phosphoester analog bonds, such as thioester bonds, etc.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," particularly when modified with an adverb such as "highly," may refer to sequence similarity, which may or may not relate to a common evolutionary origin.

In a specific embodiment, two DNA sequences are "substantially homologous" or "substantially similar" when at least about 80% (preferably at least about 90%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A nucleic acid comprising one or more of segments A, B, and C, including an enhancer element (comprising all three segments in proximity), can be isolated from any source, particularly from a human genomic library. Methods for obtaining such nucleic acids are well known in the art, as described above (see, e.g., Sambrook et al., 1989, supra). Accordingly, any human cell potentially can serve as the nucleic acid source for the molecular cloning of a regulatory element. The DNA may be obtained by standard procedures known in the art from cloned DNA (e.g., a DNA "library").

Once the DNA fragments are generated, identification of the specific DNA fragment containing the desired regulatory activity may be accomplished in a number of ways. For example, as shown in the Examples, regulation of expression of a reporter gene, such as luciferase, can establish that the regulatory element or elements have been obtained. Alternatively, oligonucleotide probes or primers can be used to detect the presence of a nucleic acid encoding the regulatory region. As noted above, the greater the degree of sequence similarity, the more stringent hybridization conditions can be used.

The present invention also relates to cloning or using recombinant means to prepare vectors containing genes encoding analogs and derivatives of the regulatory segments of the invention, that have the same or homologous functional activity as the segments, and homologs thereof from other species. Also contemplated, and specifically exemplified herein, are derivatives or analogs of the regulatory segments that do not bind to the specific proteins. Such "non-functional" derivatives or analogs can be used to evaluate the characteristics of the DNA binding proteins that recognize the regulatory segments of the invention. The production and use of derivatives and analogs are within the scope of the present invention.

Nucleic acids encoding derivatives and analogs of the invention can be produced by various methods known in the art. The manipulations which result in their production can occur at the gene or protein level. For example, the cloned regulatory segment can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. Additionally, the regulatory segment can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., J. Biol. Chem. 253:6551, 1978; Zoller and Smith, DNA 3:479488, 1984; Oliphant et al., Gene 44:177, 1986; Hutchinson et al., Proc. Natl. Acad. Sci. U.S.A. 83:710, 1986), use of TAB™ linkers (Pharmacia), etc. PCR techniques are preferred for site directed mutagenesis (see Higuchi, "Using PCR to Engineer DNA", in PCR Technology: Principles and Applications for DNA Amplification, H. Erlich, ed., Stockton Press, 1989, Chapter 6, pp. 61–70).

A regulatory element of the invention can be inserted into an appropriate expression vector, i.e., a vector which contains the necessary elements for the transcription and translation of a protein-coding sequence. Thus, the regulatory element of the invention is operatively associated with a gene in an expression vector of the invention. Both cDNA and genomic sequences can be cloned and expressed under control of such regulatory sequences. An expression vector also preferably includes a replication origin.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant gene may be expressed chromosomally under control of a regulatory element of the invention after integration of the coding sequence by recombination. In this regard, any of a number of amplification systems may be used to achieve high levels of stable gene expression (See Sambrook et al., 1989, supra).

Any of the methods for the insertion of DNA fragments into a cloning vector may be used to construct expression vectors. These methods may include in vitro recombinant DNA and synthetic techniques and in vivo recombination (genetic recombination).

Expression of a protein under control of a regulatory element of the invention may be controlled by any promoter known in the art, so long as the promoter is functional in the host selected for expression. Promoters which may be used to control gene expression include, but are not limited to, the cytomegalovirus immediate early (CMV) promoter, the SV40 early promoter region (Benoist and Chambon, Nature 290:304–310, 1981), the promoter contained in the 3' long terminal repeat of Rous sarcoma virus (Yamamoto, et al., Cell 22:787–797, 1980), the herpes thymidine kinase promoter (Wagner et al., Proc. Natl. Acad. Sci. U.S.A. 78:1441–1445, 1981), and the regulatory sequences of the metallothionein gene (Brinster et al., Nature 296:3942, 1982). In specific embodiments, the regulatory element of the invention is operably associated with an HSVtk promoter and with a $\beta_3$-AR promoter. In a preferred embodiment, a heterologous gene is expressed under control of a $\beta_3$-AR promoter.

Vectors are introduced into the desired host cells by methods known in the art, e.g., transfection, electroporation, microinjection, transduction, cell fusion, DEAE dextran, calcium phosphate precipitation, lipofection (liposome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Gene Therapy and Transgenic Vectors

As discussed above, a vector is any means for the transfer of a nucleic acid according to the invention into a host cell. The regulatory elements of the present invention, which permit positive, tissue-specific expression control, are useful in conjunction with delivery of a therapeutic gene in vivo or ex vivo, e.g., gene therapy. Such vectors can be viral vectors, such as retroviruses, herpes viruses, adenoviruses and adeno-associated viruses, or non-viral vectors.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques 7:980–990, 1992). Preferably, the viral vectors are replication defective, that is, they are unable to replicate autonomously in the target cell. In general, the genome of the replication defective viral vectors used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion, or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Thus, a specific tissue can be specifically targeted. Examples of particular vectors include, but are not limited to, a defective herpes virus 1 (HSV1) vector (Kaplitt et al., Molec. Cell. Neurosci. 2:320–330, 1991), defective herpes virus vector lacking a glyco-protein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (J. Clin. Invest. 90:626–630, 1992; see also La Salle et al., Science 259:988–990, 1993); and a defective adeno-associated virus vector (Samulski et al., J. Virol. 61:3096–3101, 1987; Samulski etal., J. Virol. 63:3822–3828, 1989; Lebkowski et al., Mol. Cell. Biol. 8:3988–3996, 1988).

Adenovirus vectors.

Adenoviruses are eukaryotic DNA viruses that can be modified to efficiently deliver a nucleic acid of the invention to a variety of cell types. Various serotypes of adenovirus exist. Of these serotypes, type 2 or type 5 human adenoviruses (Ad 2 or Ad 5) or adenoviruses of animal origin (see WO94/26914) are most commonly used. Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors of the invention comprise the inverted terminal repeats (ITRs), an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649, WO95/02697 and WO96/22378), or in any of the late genes L1-L5.

The replication defective recombinant adenoviruses according to the invention can be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence of interest. The homologous recombination is effected following cotransfection of the adenovirus and plasmid into an appropriate cell line. The cell line which is employed should preferably (i) be transformable by the elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., J. Gen. Virol. 36 (1977) 59) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Adeno-associated Viruses.

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions which carry the encapsidation functions: the left-hand part of the genome, which contains the rep gene involved in viral replication and expression of the viral genes; and the right-hand part of the genome, which contains the cap gene encoding the capsid proteins of the virus. The use of vectors derived from the AAVs for transferring genes in vitro and in vivo has been described (see WO 91/18088; WO 93/09239; U.S. Pat. Nos. 4,797,368, 5,139,941, EP 488 528).

Retrovirus Vectors.

In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, Eβ178220; Bernstein et al. Genet. Eng. 7:235, 1985; McCormick, BioTechnology 3:689, 1985; International Patent Publication No. WO 95/07358, published Mar. 16, 1995, by Dougherty et al.; and Kuo et al., 1993, Blood 82:845. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697. Packaging cell lines for preparation of retroviral vectors have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the long terminal repeats (LTRs) for suppressing transcriptional activity as well as extensive encapsidation sequences which may include a part of the gag gene (Bender et al., J. Virol. 61:1639, 1987). Recombinant retroviral vectors are purified by standard techniques known to those having ordinary skill in the art.

Non-viral Vectors.

Alternatively, the vector can be introduced in vivo as naked DNA, or with a DNA transfer facilitating agent, such as a lipid.

For example, one method for transfer of a nucleic acid vector is by lipofection. Synthetic cationic lipids designed to limit the difficulties and dangers encountered with liposome mediated transfection can be used to prepare liposomes for in vivo transfection of a gene encoding a marker (Felgner, et. al., Proc. Natl. Acad. Sci. U.S.A. 84:7413–7417, 1987; see Mackey, et al., Proc. Natl. Acad. Sci. U.S.A. 85:8027–8031, 1988; Ulmer et al., Science 259:1745–1748, 1993). The use of cationic lipids may promote encapsulation of negatively charged nucleic acids, and also promote fusion with negatively charged cell membranes (Felgner and Ringold, Science 337:387–388, 1989). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting (see Mackey, et. al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/2193 1), peptides derived from DNA binding proteins (e.g., International Patent Publication WO96/25508), or a cationic polymer (e.g., International Patent Publication WO95/2193 1).

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., J. Biol. Chem. 267:963–967, 1992; Wu and Wu, J. Biol. Chem. 263:14621–14624, 1988; Hartmut et al., Canadian Patent Application No. 2,012,311, filed Mar. 15, 1990; Williams et al., Proc. Natl. Acad. Sci. USA 88:2726–2730, 1991). Receptor-mediated DNA delivery approaches can also be used (Curiel et al., Hum. Gene Ther. 3:147–154, 1992; Wu and Wu, J. Biol. Chem. 262:4429–4432, 1987).

Screening Assays

Identification and isolation of the regulatory elements of the invention provides for development of screening assays, particularly for high throughput screening of molecules that up- or down-regulate the activity of the regulatory element of the invention. In one embodiment, control of the regulatory element can be effected by increasing or decreasing the activity of a trans-acting factor (preferably the B-segment-binding trans-acting factor) of the invention. Alternatively, the factor can act directly by interacting with the sequences of the regulatory segments or region.

Molecules that increase the activity of the regulatory element of the invention, and thus increase the level of expression of endogenous $\beta_3$-AR, would be useful in combination with a $\beta_3$-AR-specific agonist for the treatment of obesity and diabetes, particularly non-insulin dependent diabetes mellitus (NIDDM). In particular, an agent that induces expression of the B-segment-specific trans-acting factor discovered herein would be useful for inducing $\beta_3$-AR expression in a desired tissue, such as a WAT cell or an undifferentiated adipocyte (so as to push it to differentiation into a BAT cell), so as to render it sensitive to a $\beta_3$-AR agonist. In addition, such agents may be useful in combination with a $\beta_3$-AR agonist for treating urinary incontinence and to suppress ureteral colic; in the facilitation of stone discharge in urolithiasis patients; and in the treatment of depression (at least one $\beta_3$-AR agonist having been shown to have anti-depressant activity).

Any mammalian cell can be used to screen for molecules that increase or decrease the activity of a $\beta_3$-AR trans-activating factor. Preferably the cells express or have the potential to express the $\beta_3$-AR trans-activating factor, such as BAT (including HIB) or SK-N-MC cells. BAT and SK-N-MC cells have been discussed. The HIB 1B cell line was derived from brown adipose tissue (BAT) tumor isolated from transgenic mice (Ross et al., PNAS, 89:7561–7565, 1992). This cell line represents the first established brown adipocytes cell line capable of expressing uncoupling protein 1 (UCP-1). UCP-1 is a mitochondrial protein expressed exclusively in BAT. UCP-1 mRNA is detectable after stimulation of $\beta$-adrenergic receptor system that is present in these cells ($\beta_1$- and $\beta_2$-AR, 60 –70%, and $\beta_3$-AR, 30 –40%) (Klaus et al., J. Cell. Sci., 107:313–319, 1994). The HIB 1B cells are maintained in DMEM:F12 (1:1) in the presence of 10% FCS. When they reach confluency, cells are induced to differentiate (i.e., to show UCP-1 expression and accumulation of lipid droplets). Differentiation is achieved by adding 5% FBS in addition to $T_3$ and insulin, to the medium. Seven days after confluency in the presence of $T_3$ and insulin, 90–95% of the cells are differentiated.

Any screening technique known in the art can be used to screen for compounds that up- or down-regulate the activity of the regulatory region of the invention. As used herein, the term "compound" refers to any molecule or complex of more than one molecule that affects the regulatory region. The present invention contemplates screens for synthetic small molecule agents, chemical compounds, chemical complexes, and salts thereof as well as screens for natural products, such as plant extracts or materials obtained from fermentation broths. Other molecules that can be identified using the screens of the invention include proteins and peptide fragments, peptides, nucleic acids and oligonucleotides (particularly triple-helix-forming oligonucleotides), carbohydrates, phospholipids and other lipid derivatives, steroids and steroid derivatives, prostaglandins and related arachadonic acid derivatives, etc.

Knowledge of the primary sequence of the regulatory region, and particularly the regulatory segments, permits development of DNA binding molecules, including triple-helix forming oligonucleotides, that can be used to interfere with transcription factor binding to the regulatory region, and thus inhibit or block positive gene regulation mediated by the region.

Various approaches can be used to identify small molecules for testing. One approach uses primarily chemical methods, of which the Geysen method (Geysen et al., Molecular Immunology 23:709–715, 1986; Geysen et al., J. Immunologic Method 102:259–274, 1987) and the method of Fodor et al. Science 251:767–773, 1991) are examples. Furka et al. (14th International Congress of Biochemistry, Volume 5, Abstract FR:013, 1988; Furka, Int. J. Peptide Protein Res. 37:487–493, 1991), Houghton (U.S. Pat. No. 4,631,211, issued Dec. 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., Proc. Natl. Acad. Sci. USA 90:10700–4, 1993); Ohlmeyer et al., Proc. Natl. Acad. Sci. USA 90:10922–10926, 1993); Lam et al., International Patent Publication No. WO 92/00252; Kocis et al., International Patent Publication No. WO 9428028) and the like can be used to screen for agents according to the present invention.

Reporter Gene Assays

The screening can be performed with recombinant cells that express a reporter gene under control of the regulatory region of the invention, particularly the enhancer region. For example, in an example, infra, luciferase (a reporter gene) is placed under control of the enhancer region for detecting enhancement of reporter gene expression.

In one embodiment, a reporter gene assay can be used to detect increased expression of a gene under control of the $\beta_3$-AR enhancer element in a cell that does not normally express or expresses at very low levels $\beta_3$-AR relative to $\beta_3$-AR-expressing cells. Such cells include WAT cells (including perirenal cells), muscle cells, liver cells and HeLa and CV-1 cells. In a specific embodiment, mouse WAT, muscle, and liver cells did not express the B segment trans-activating factor. These cells, recombinantly engineered with a reporter gene under control of the enhancer region, can be used to screen for molecules that induce trans-activating factor activity.

In another embodiment, increased levels of expression of the B segment binding trans-activating factor can be detected in cells that express $\beta_3$-AR, including but not limited to BAT cells (including HIB cells, which is a BAT-derived cell line), and human neuroblastoma cells. In both cases, an increase in the level of expression of the reporter gene, relative to the level of expression in the absence of a test compound, indicates that the test compound has a positive influence on regulation of expression under control of the regulatory element of the invention.

Alternatively, a reporter gene assay can be used to test inhibitors of the regulatory region. Such reporter gene assays are most conveniently performed on cells that constitutively express high levels of a reporter gene operatively associated with the regulatory element. A reduction in the level of expression of the reporter gene in the presence of a test compound, relative to the level of expression in the absence of the test compound, indicates that the test compound inhibits expression control by the regulatory element.

Reporter genes for use in the invention encode detectable proteins, including, but are by no means limited to, chloramphenicol transferase (CAT), β-galactosidase (β-gal), luciferase, green fluorescent protein, alkaline phosphatase, and other genes that can be detected, e.g., immunologically (by antibody assay).

Direct Assays for B Segment Binding Trans-Activating Factor Activity

As an alternative or an adjunct to the reporter gene assays described above, the present invention permits directly assessing the level of expression of the B segment binding trans-activating protein by detecting the amount of this protein associated with a nucleic acid containing the B segment core binding sequence. Such assays include gel shift assays, solid phase binding assays, and the like.

For such assays, preferably either the nucleic acid (such as an oligonucleotide) containing the B segment sequence, or the protein, or both, are detectably labeled so that any binding of the two can be detected. Such labels include enzymes, such as alkaline phosphatase and horseradish peroxidase; colored latex beads; magnetic beads; fluorescent labels, e.g., fluorescein isothiocyanate (FITC), phycoerythrin (PE), Texas red (TR), rhodamine, free or chelated lanthanide series salts, especially $Eu^{3+}$, to name a few fluorophores; fluorescence transfer pairs; chemiluminescent molecules; radioisotopes; or magnetic resonance imaging labels. In a specific embodiment, the oligonucleotide is radiolabeled.

Isolation and Characterization of the B Segment Trans-Activating Factor

A significant and unexpected discovery of the present invention is the identification and characterization of a novel AP-2-like transcription factor, the B-segment binding trans-activating factor. This factor binds to DNA having the sequence GCCTCTGGGGAG (SEQ ID NO: 1), and is expressed, inter alia, by mouse brown adipose tissue cells and the human neuroblastoma cell line SK-N-MC; it is also expressed at very low levels in perirenal white adipose tissue (and perhaps not at all in pure white adipose tissue cells), and an AP-2 oligonucleotide does not compete with the B segment sequence for binding to this factor. Furthermore, the factor is not recognized by an anti-AP-2 antibody. Although the presence and characteristics that permit unambiguous identification of this factor are set forth herein, the invention advantageously permits further evaluation and characterization, including elucidation of the sequence of the gene encoding the factor, and accordingly deduction of the complete amino acid sequence.

The transcription factor AP-2 was first isolated from HeLa cells by affinity chromatography and subsequently cloned by screening a HeLa genomic library. AP-2 is a 52 kDa protein which gene was mapped to a region on chromosome 6. The DNA binding domain within AP-2 transcription factor is located in C-terminal half of protein and consists of two putative amphipathic alpha helices separated by a large spanning region. The N-terminal domain of AP-2 protein contains a trans-activation domain with a proline-rich region. AP-2 transcription factor binds to a consensus binding site -5'-GCCNNNGGC-3' (SEQ ID NO: 4) that is found in numerous viral and cellular promoters. Activity of AP-2 is regulated by different agents. Phorbol-ester and agents that lead to an increase of cAMP induces AP-2 activity independently of protein synthesis (Buttner et al., Mol. Cell. Biology, 13:4174–4185, 1993; Bauer et al., Nucleic Acid Research, 22:1413–1420, 1994.)

Various means can be used to isolate the B segment binding factor protein or gene, including a yeast one-hybrid assay in a system recombinantly engineered to express polypeptides from cells that express the $β_3$-AR. Such cells include BAT cells (including HIB cells), and human neuroblastoma cells, such as SK-N-MC cells. The yeast one hybrid system was described by Fields and Song (Nature, 340:245–247, 1989). Numerous laboratories have used this system to successfully clone unknown transcription factors that bind for identified DNA binding sites (e.g., Wu et al., EMBO J., 13:4823–4830, 1994). The yeast-one hybrid system provides the tool for isolation of novel genes that encode the proteins that bind to a target: cis-acting regulatory DNA elements. The one-hybrid assay is based on the interaction between a target-specific DNA-binding domain and a target-independent activation domain (AD). The binding domain for target DNA is provided in a construct with the AD. If the binding protein that recognizes the target DNA is present in the cDNA library, its expression will allow binding to target DNA. Binding to the target DNA results in expression and binding of AD to transcriptional machinery of another vector to induce expression of a reporter gene.

Three copies of oligonucleotides that correspond to region B are synthesized, annealed and cloned into the Eco RI and the Mlu I sites of pHISi, pHISI-1 and pLacZi vectors (Clontech). B/pHISi and B/pHISi-1 clones are then stably transfected into the genome of yeast strain YM4271. The yeast cells are transformed according to established protocol using LiAc method and colonies selected by growth on SD-His plates. To confirm that the clones have stably integrated B/pHISi or B/pHISi-1 plasmids, colonies are picked and lysed, and PCR is performed using primers on each side of the insert flanking the NcoI site. PCR products that contain the proper size insert are considered positive. The B/pHISi/YM4271 stably integrated yeast cells are transformed with a mouse brown adipose tissue (BAT) library constructed into a pGAD10 vector (custom-made library by Clontech). Colonies are selected by growth on SD/-his/-leu plates supplemented with 30 mM 3-AT (3-amino-1,2,4-triazole). Larger colonies which grow up are streaked onto grid plates and a P-galactosidase assay is performed by colony lifts according to the manufacturer's protocol. PCR is performed on lysed yeast colonies using primers flanking the insert region of the pGAD1 vector. PCR products containing inserts are ligated using T-A cloning system into pCRII vector. Colonies that contain inserts are sequenced and subjected to BLAST search.

Screening of an expression library generated from SK-N-MC poly-A RNA with a radiolabeled segment "B" oligonucleotide is another strategy for cloning and isolation of the transcription factor that binds for "B" sequence.

Alternatively, a nucleic acid, and particularly a DNA oligonucleotide, comprising the B segment core binding sequence GCCTCTGGGGAG (SEQ ID NO: 1) can be used to isolate the protein, e.g., by an affinity chromatography technique. Alternatively, such an oligonucleotide can be used to capture polysomes expressing the B segment binding factor, permitting isolation and reverse cloning of the B segment binding factor mRNA.

The present invention will be better understood by reference to the following Example.

DESCRIPTION OF THE PREFERRED EMBODIMENTS

The Examples in this application are intended to be exemplary thereof, and are not intended to be limiting.

EXAMPLE 1

Isolation and Characterization of a $\beta_3$-AR Enhancer

This example presents data that show the existence of h$\beta_3$-AR cis-acting positive regulatory elements between −6.5 kb to −6.3 kb of the 5'-flanking region. These positive regulatory elements consist of three DNA binding sequences: A, B, and C that act synergistically. Region A binds Sp1 binding factor, region B is recognized by proteins (as yet unidentified) present in nuclear extracts from SK-N-MC cells as well as mouse BAT, and region C is represented by 20 repeats of a CCTT motif that is necessary to achieve full transcriptional activity of h$\beta_3$-AR enhancer.

Materials and Methods

Cloning of Human $\beta_3$-AR Genomic DNA.

In order to isolate a 5'-flanking region of the h$\beta_3$-AR gene, a Human Fibroblast Genomic Library (Stratagene, LaJolla, Calif.) was screened using a 1.2 kb insert from cDNA for the h$\beta_3$-AR gene cDNA was constructed by ligating four polymerase chain reaction (PCR) products using the following primers: an ATG-NarI fragment, sense primer 5' CTTTC-CCTACCGCCCACGCGCGATC 3' (SEQ ID NO: 5) and anti-sense primer 5' GTGGCGCCCAACGGCCAGTGG-CAGTC 3' (SEQ ID NO: 6); a NarI-AccI fragment, 5' TTGGCGCTGACTGGCCACTGGCCGTTG 3'(SEQ ID NO: 7) as sense and 5' GCGCGTAGACGAAGAGCAT-CACGAG 3' (SEQ ID NO: 8) as anti-sense primer; an AccI-StyI fragment, sense primer 5' CTCGTGATGCTCT-TCGTCTSCGCGC 3' (SEQ ID NO: 9) and anti-sense primer 5' GTGAAGGTGCCCATGATGAGACCCAAGG 3' (SEQ ID NO: 10) and a StyI-TAG fragment, with sense primer 5' CCCTGTGCACCTTGGGTCTCATCATGG 3' (SEQ ID NO: 11) and anti-sense primer 5' CCTCTGC-CCCGGTTACCTACCC 3' (SEQ ID NO: 12). The corresponding primer sequences were taken according to Emorine et al. (Science 245:1118–21).

The four fragments were ligated into a pUC 18 plasmid (Gibco-BRL) and sequenced. Using cDNA as a probe two genomic clones were isolated. In addition a PCR product representing a 1.3 kb h$\beta_3$-AR promoter that was previously published (Liggett et al., J. DNA Sequencing and Mapping 2:61–63, 1991) was used to identify and map 7 kb of the h$\beta_3$-AR gene 5'-flanking region. This 7 kb promoter region was subcloned into pSP 72 (Promega, Madison, Wis.) between PstI and HindIII restriction enzyme sites and mapped extensively. The full length of the promoter was sequenced in both directions using automated sequencing with primers designed to "walk" along the sequence as further sequences were obtained.

5' RACE.

To identify the transcription start site of the h$\beta_3$-AR gene, 5' RACE was performed using SK-N-MC cell total RNA purified using RNAzol B (Tel-Test, Inc., Friendswood, Tex.). Poly A RNA was then purified using an Ambion Micropo(A) pure kit. The 5' RACE was done using the Marathon cDNA amplification kit (Clonetech, Palo Alto, Calif.) according to the protocol provided with the kit. The primers used included: the sense adapter primer AP2 (Clonetech) 5' ACTCACTATAGGGCTCGAGCGGC 3' (SEQ ID NO: 13) and antisense primer 5' GGCAGC-CCACTGGTGTTGGCGGTAT 3' (SEQ ID NO: 14) that corresponded to the h$\beta_3$-AR gene sequence at positions 729–703 as per the sequence from GenBank with accession # X72861 (positioned 81 base pairs in the 5'-3' direction from the translation start site). The PCR products were then cloned into a pCRII vector using the TA cloning kit (Invitrogen, Carlsbad, Calif.). The clones were sequenced using the ABI 373 Automated Sequencer.

Human $\beta_3$-AR Gene Promoter Deletion Constructs.

Serial deletions of the h$\beta_3$-AR gene 5'-flanking region were designed in order to identify the region(s) responsible for transcriptional regulation. A 7 kb sequence was subcloned into the KpnI/HindIII sites of a pGL3 basic vector (Promega) to obtain the full length promoter to drive expression of the reporter gene luciferase labeled here as −7 h$\beta_3$/Luc (KpnI is a part of a multiple cloning site from pSP72) pGL3 basic contains luciferase cDNA as a reporter gene and an upstream synthetic poly-A signal to reduce background. The deletion constructs labeled as −5.5h$\beta_3$/Luc, −3h$\beta_3$/Luc and 0.5h$\beta_3$/Luc were made by digestion with AvrII, EcoRV and BstEII, respectively and KpnI, blunt ended and re-ligated. The construct −0.3h$\beta$3/Luc was made by ligating a PCR product corresponding to a 1.3 kb region of the h$\beta$3-AR gene promoter that has been previously published (Liggett and Schwina, supra). The PCR product was obtained using HeLa cell genomic DNA and the 5' ggtaccTCTAGGTGGAAAGGTGCATG 3' (SEQ ID NO: 15) as sense and 5' aagcttAGTCCCCTCCCTGTCGT 3' (SEQ ID NO: 16) as anti-sense primers (GenBank sequence with accession #M62473) was used when choosing the primers.

Constructs with deletions in the promoter region were made as follows: for the dEVh$\beta$3AR/Luc parental vector −7h$\beta_3$AR/Luc was digested with Avr II (−5.6 kb) and EcoRV (−3.1 kb), blunt ended and re-ligated; for dEIh$\beta_3$AR/Luc, a deletion between Avr II and EcoRI (=2.3 kb) was made, and dBh$\beta_3$AR/Luc was made by digestion of the parental vector with Avr II and BstEII (−0.5 kb); sites of digestion were blunt ended and re-ligated.

To further analyze and more precisely identify the sequence located between −7 kb and −5.6 kb of the h$\beta_3$-AR promoter that contains cis-regulatory elements, expression plasmids were generated containing PCR products made using a series of primers shown in Table 1.

TABLE 1

PCR Primers for Analysis of the hβ₃-AR Promoter

| Primer No. | Primer Sequence | Amplified Genome Region | SEQ ID NO. |
|---|---|---|---|
| *Sense Primers* | | | |
| 1S | 5'CTGCAGGGGTTGAGAAC3' | (−7.12 KB—7.107 kb) | 17 |
| 3S | 5'gctagcGCAAGTGCAATCTATAACACAGGGG3' | (−6.96 kb—6.94 kb) | 18 |
| *Antisense Primers* | | | |
| 4AS | 5'gtcgacGCTGGGATTACAGGTCCGTGC3' | (−6.71 kb—6.69 kb) | 19 |
| 6AS | 5'gtcgacATGCTTAGGCTTCCTTCCAGG3' | (−6.50 kb—6.48 kb) | 20 |
| 8AS | 5'gtcgacCTTTTGCAAGTGGCACGAAGG3' | (−6.32 kb—6.30 kb) | 21 |
| 14AS | 5'gtcgacACCTGCCAGTCTGCCTTCTC3' | (−5.90 kb—5.82 kb) | 22 |
| 12AS | 5'gtcgacCCTAGGTGGCAGAGCGAGACTCT3' | (−5.64 kb—5.62 kb) | 23 |

Notes to Table 1:
Sequences of primers used in PCR to make vectors that contain regions necessary for transcription of hβ₃-AR. Position of primers were determined from the translation start site as +1. Small letters represent Kpn I and Nhe I restriction enzyme sites introduced within sense and anti-sense primers, respectively.

The PCR fragments were further ligated either in front of the HSV TK as a minimal promoter or 0.5 kb proximal to the hβ₃-AR gene promoter as an endogenous minimal promoter. Using −7 Kbhβ3AR/Luc in pGL3 Basic as a template, PCR was performed with primer sets shown in Table 1, in which the sense primers contained an NheI restriction enzyme site and antisense primers contained a SalI restriction site for cloning purposes. PCR conditions were: 94° C. 2 min, 94° C. 45 sec, 57° C. 45 sec, 72° C. 45 sec with 25 cycles and 72° C. 7 min extension. Amplified fragments were cloned into a pCRII vector (Invitrogen). The TK minimal promoter was obtained from plasmid pTKb (Clontech) using BglII and SalI to excise it. The TK fragment was subcloned into pSP72 (Promega) SalI/BglII sites. PCR products were digested with HindIII/SalI, gel purified and ligated into pSP72 containing the TK minimal promoter. After digestion with NheI/BglII, PCR products/TK minimal promoter were gel purified and cloned back into the pGL3 basic. As a measure of basal transcriptional activity, the construct containing TK-minimal promoter in pGL3 basic was transfected into both SK-N-MC and CV-1 cells. Data from experiments were expressed as fold increase over TK/pGL3 activity. All clones were confirmed by sequencing.

When 0.5 kb of the endogenous gene was used as a minimal promoter, primers containing a KpnI site introduced in sense orientation and a BstEII site in anti-sense orientation were used. PCR products excised with KpnI and BstEII were ligated in front of −0.5hβ3AR/Luc constructs. Primers used were as follows: sense 5' ggtaccGCAAGTG-CAATCTATAACACAGGGG 3' (SEQ ID NO: 24) and antisense 5' ggttaccCTTTTGCAAGTGGCACGAAGG 3' (SEQ ID NO: 25). PCR products between primers "3S× 12AS", "3S×14AS" and "3S×8AS", were also ligated in the reverse orientation in front of a TK minimal promoter.

In order to examine in more detail the importance of specific cis-elements identified as potential regulators of transcription of the human β₃-AR gene, DNA constructs were made that contained mutations in segments A and/or B, keeping segment C intact in the context of the "3×8" −0.5hβ3AR/luc. The importance of segment C was examined by deleting the whole segment from the constructs containing segments A and B, or examining the transcriptional activity when segment C alone was present, i.e., construct C-0.5 β3/Luc. To introduce mutations within these constructs, PCR primers were designed that contained mutations within segments A and/or B that do not bind SK-N-MC cell nuclear extracts as previously established in our EMSA experiments. Conveniently, a unique BssSI site exists at position −6.46 kb immediately after the sequence within segment A where mutation caused a loss of binding. Region "3×8", with or without mutation within segment A, was digested with BssSI to which segment B generated PCR products (with or without mutation) were ligated. Briefly, to generate "3×8", A mutated (m), B, C, primer number "3" as sense (see Table 1) and primer 5' GTTGTTCCTGG-GACTCGTGA 3' (SEQ ID NO: 26) (introduced mutation is bold and BssSI site is underlined) as antisense were used. PCR products were digested with KpnI and BssSI and ligated into "3×8" 0.5hβ3/luc previously digested with the same enzymes. To generate both "3×8" A, Bm, C and "3×8" Am, Bm, C, which contains a mutation in the B-segment, sense primer 5' TGGGACTCGTGACCTCTCCCAGCCA-GACGGGAGC 3' (SEQ ID NO: 27) (which introduced a mutation in the B-segment indicated by bold text) and antisense primer number "8" (see Table 1) were used to make PCR products that were subsequently digested with BssSI/BstEII and ligated into previously BssSI/BstEII digested plasmids "3×8" 0.5β3/luc and "3×8" Am, B, C respectively.

Cell Culture.

Three cell lines were used in these experiments: SK-N-MC cells, a human neuroblastoma cell line that endogenously expresses β₃-ARs as well as β₁-ARs (Granneman et al., Mol. Pharmacol. 42:964–970, 1992) (ATCC, Manassas, Va.); CV-1 kidney cells from the green monkey; and HeLa cells. Cells were grown in mono-layers in media recommended by ATCC (ME) for SK-N-MC cells supplemented with 10% fetal bovine serum (FBS;Gibco, BRL). The CV-1 cells were grown in DMEM (10% FBS), while HeLa cells were maintained in F-12 (GIBCO, BRL) supplemented with 10% FBS. All media also contained penicillin (100 units/ml) and streptomycin (100 mg/ml). Cells were grown at 37° C. with 5% $CO_2$.

Transient Transfection Experiments.

DNA constructs were transiently transfected into cells using either calcium phosphate precipitation or lipofect NE-plus addition. Both products were obtained from Gibco-BRL. Cells were transfected in a condition of subconfluency. Three hours before transfection, media was changed. Transient transfection using the $CaPO_4$ method was done as recommended by Gibco. Ten μg of construct containing luciferase as a reporter gene and 1 μg of pRSVβ-gal (Clontech) as a control for transfection efficiency were used. On some occasions, lipofectAMINE-plus was used. Briefly, 1.5 μg of the DNA constructs per well and 0.17 μg of pSVβ-gal for transfection efficiency correction were used. The DNA constructs, reagent and Optimem® were mixed and incubated at room temperature for 15 min. Lipofectamine and 100 μl Optimem® were mixed, combined with DNA, and incubated at room temperature for 15 min; 200 μl of the transfection mix was added to each well containing 3 μl of Optimem®. After incubation for 16 hrs at 37° C. and 5% $CO_2$, the media was replaced and incubated an additional 24 hrs. The next day cells were assayed for luciferase and β-galactosidase (β-gal) activity. In each experiment all constructs were tested in triplicate. Each experiment was repeated 4–5 times with 2–3 different DNA preparations. Two different passages of SK-N-MC cells were tested.

The luciferase activity was determined as previously described (Hollenberg et al., The Journal of Biological Chemistry 272:5283–5290, 1997). β-gal activity was measured using a Tropix kit (Cambridge, Mass.).

Nuclear Extracts and Electrophoretic Nobility Shift Assay.

Nuclear extracts were isolated from SK-N-MC and CV-1 cells as well as from mouse BAT, WAT, liver and muscle tissue. Nuclear extract from HeLa cells was purchased from Promega. For isolation, a method described previously was used (Latchman, D. S., Transcription Factors A Practical Approach, Oxford University Press, Oxford 1–13). Cells that were 80–90% confluent were washed three times with PBS buffer, and incubated with buffer A composed of 10 mM Hepes pH 7.9, 1.5 mM $MgCl_2$, 10 mM KCl, 0.5 mM DTT, 0.5 mM PMSF and a cocktail of several protease inhibitors (Boeheringer Mannheim, Indianapolis, Ind.). After a 10 min. incubation on ice, cells were centrifuged for 10 min at 250× g. Pellets were resuspended in 3 volumes of ice-cold buffer A with 0.05% Nonident P-40, and homogenized with 20 strokes in a Dounce homogenizer. After centrifugation, pellets were resuspended in buffer B containing 5 mM Hepes, pH 7.9, 26% glycerol v/v, 1.5 mM $MgCl_2$, 0.2 mM EDTA, 0.5 mM DTT, 0.5 mM PMSF and a cocktail of protease inhibitors. NaCl was added to a concentration of 300 mM, and the suspension was incubated 30 min. on ice. After centrifugation at 24000× g for 50 min., supernatants were aliquoted and stored at –70° C. Protein concentration was measured using the Bradford reagent (Biorad, Hercules, Calif.).

Nuclear extracts were isolated from tissue using the method of Varshavsky (Meth. Enzymology, 151:551–565, 1987). Tissues of interest (BAT; WAT, liver and muscle) were isolated from mice and placed in ice cold PBS. All procedures were done at 4° C. Tissues were weighed, minced, and homogenized in buffer A: 15 mM Hepes pH7.6, 60 mM KCl, 15 mM NaCl, 0.25 mM $MgCl_2$, 0.5 mM EGTA, 0.5 mM spermine, and protease inhibitor cocktail. Nonidet-P-40 was added at a final concentration of 0.05% for BAT, liver and muscle and 0.2% for WAT. Tissue homogenates were centrifuged at 1200× g for 10 min. Pellets were resuspended in 0.3 M Sucrose/buffer A and layered in an equal volume on a cushion of 1.7M Sucrose/buffer A. After centrifugation, pellets were resuspended in 1 ml buffer B: 10 mM Hepes pH 7.6, 350 mM NaCl, 5% Glycerol, 1.5 mM $MgCl_2$, 0.1 mM EGTA and protease inhibitor cocktail, and incubated at 4° C. for 30 min. After centrifugation at 100,000× g for 60 min, supernatants were aliquoted, stored at –70° C. and protein concentration determined.

All crude nuclear extracts were further purified using a heparin column as described previously (McPherson et al., Proc. Natl. Acad. Sci. USA, 94:4342–4347, 1997). Crude extracts were diluted in appropriate buffer to make a final concentration of 20 mM Hepes pH 7.9, 20% glycerol, 150 mM KCl/$NaCl_2$, 2 mM $MgCl_2$, 0.2 mM EDTA and protease inhibitor cocktail. The Heparin Sepharose CL-6B column (Pharmacia Biotech, Uppsala, Sweden) was made from a 50% slurry of about 1 ml. The columns were equilibrated with 10 ml of the equilibration buffer described above. Crude nuclear extracts were loaded onto columns and flow-through collected. After columns were washed, proteins were eluted with elution buffer (same as dilution buffer described above only containing 0.8M KCl). Aliquots of 200 ml were collected and stored at –70° C.

Electrophoretic mobility shift assays (EMSA) were done using double-stranded T4 polynucleotide kinase (Gibco-BRL) labeled oligonucleotides. Binding reactions contained 10 mg of nuclear extract protein, 1.5 mg of poly-dIdC (Pharmacia Biotech), 70,000–100,000 cpm of radiolabeled probes in a binding buffer consisting of: 0.24 mM $ZnSO_4$, 20% Glycerol, 100 mM KCl (final concentration), 0.05% Nonidet-P-40, 0.1 mM EDTA, 20 mM Hepes pH 8.4. Nuclear extract and poly-dIdC were added to the binding buffer and incubated at room temperature for 30 min. with radiolabeled probes. In some experiments cold competitor or antibodies for Sp1 and AP2 (Santa Cruz Biotechnology, Inc., Santa Cruz, Calif.) proteins were used. After incubation to allow binding, samples were run on 6% acrylamide, 0.5× TBE gel. Oligonucleotides used in EMSA are described in the text and in Figure legends. Oligonucleotides containing Sp-1 or AP2 consensus binding sites were bought from the Santa Cruz Biotechnology, Inc.

Examination of S1 Nuclease Hypersensitive Sites, and Primer Extension.

The 80 bp CCTT region of the h$β_3$-AR promoter was amplified by PCR at a position-6.508 kb to -6.488 kb of h$β_3$-AR promoter using primer number "6" 5' CCTG-GAAGGAAGCCTAAGCAT 3' (SEQ ID NO: 28) as a sense primer and primer number "16" at position –6.20 kb to –6.18 kb 5' GGCACTGCTAGGAACACACTC 3' (SEQ ID NO: 29) as an antisense primer. The PCR product was subcloned between pGEM 7, EcoRI and BglII sites that were added to PCR primers for cloning purposes. The supercoiled form of plasmid (1 μg) was digested with ScaI after 30 minutes treatment with 5 units of S1 nuclease and run on 1% agarose gel. S1 hypersensitivity was tested in the presence of increasing salt concentration as well as in different pHs. One μg of DNA was treated 30 minutes with 5U of S1 nuclease in buffer containing 50 mM Na-acetate pH 4.5, 0.1M $ZnCl_2$ and increasing concentrations of NaCl: 0, 0.05M, 0.1M, 0.3M and 0.5M, and applied to the gel. In addition, experiments were done in buffer at either pH 6 or 7 in the presence of 0.3M NaCl.

Results

Human β3-adrenergic Receptor (hβ$_3$AR) Genomic Clones.

A human fibroblast genomic library was screened using partial cDNA as a probe. Partial cDNA was generated using polymerase chain reaction (PCR) with overlapping primers to span the coding region. The PCR products were ligated and sequenced. Two positive clones were identified. The clone that contained the larger 5'-flanking region (7A) was extensively mapped using as probes exon 1 and a 1.3 kb of the hβ$_3$-AR gene promoter region previously published (Liggett and Schwin, supra). The same 1.3 kb promoter region was subcloned in a pSP72 vector, and used in further constructions and analysis. 7.0 kb of the 5' flanking region was isolated, subcloned into pSP72 and sequenced extensively from both directions using primers to "walk" along the sequence. A partial map of the hβ$_3$-AR gene with 7 kb of the 5' flanking region is shown in FIG. 1.

Identification of the Transcription Initiation Site.

Analysis of the proximal hβ$_3$-AR gene promoter using an RNase protection assay on RNA from infant brown fat and SK-N-MC cells (Granneman and Lahners, Endocrinology 135, 1025–1035, 1994) and a S1 nuclease assay (Van Spronsen et al., Eur. J. Biochem. 273:1117–1124, 1993) on RNA from human perirenal and subcutaneous adipose tissue depots suggested the existence of several transcription start sites between –200 and –130 bp proximal to the translation start site, with the strongest one being at position –180 bp upstream from the translation start site. The 5'-end of the cDNA for the hβ$_3$-AR gene was confirmed and identified using 5' RACE on poly A RNA isolated from SK-N-MC cells. Four different populations of PCR products were isolated (using a primer located 81 bp downstream from the translation start site) cloned in pCRII vector and sequenced. Sequencing showed that 6 clones stopped at position 130, 4 clones stopped at position 150, 6 clones stopped at position 200, and 4 clones stopped at position 100 from the translation start site (FIG. 2). These results are in agreement with data previously reported indicating that RNA polymerase II uses multiple transcription start sites within the promoter of the hβ$_3$-AR gene.

Analysis of –7 kb hβ$_3$-AR Promoter Regions in the hβ$_3$-AR Gene Expression.

Figure 3:
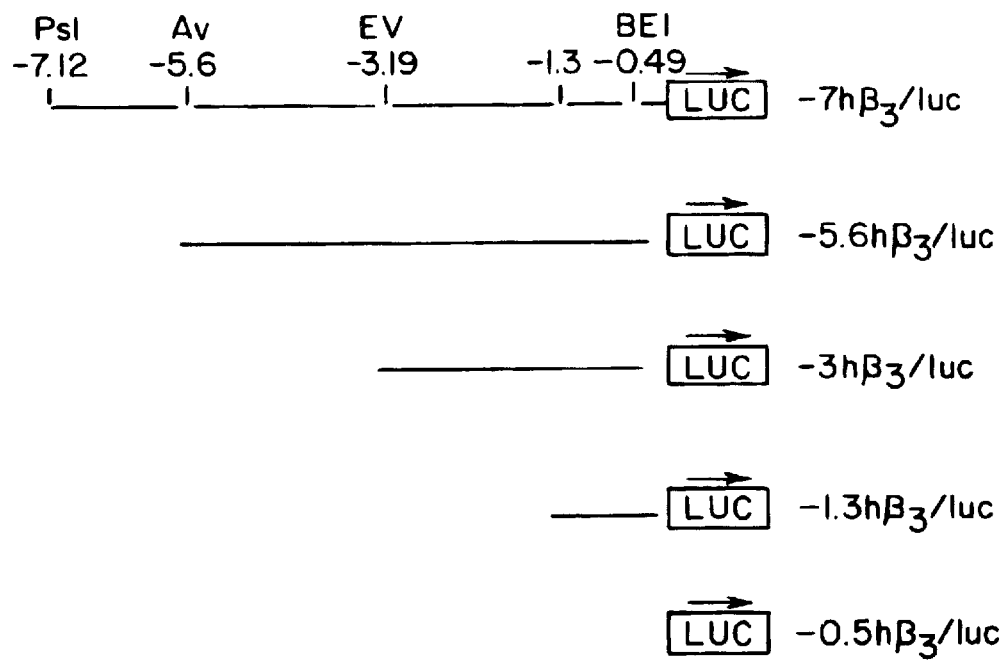
FIG. 3: Partial restriction enzymes map of constructs used in transient transfection experiments. All promoter regions were cloned in a pGL3 basic vector. The positions of the restriction enzyme sites are based on assigning the translation start site as +1.

In order to identify the location of sequences that contain regulatory elements involved in regulation of hβ$_3$-AR gene expression, serial deletions of hβ$_3$-AR promoter ligated to a luciferase reporter gene within a pGL 3 vector were made. All constructs shown in FIG. 3 were transiently transfected in SK-N-MC cells and luciferase activity measured. The data were corrected for transfection efficiency (measured as the activity of co-transfected 13-gal) and expressed as a fold increase over control plasmid (pGL3 basic) expression. The DNA construct containing only –0.5 kb of the hβ$_3$-AR promoter induced reporter gene transcription 5–6 times over basal levels, suggesting that this region contains elements sufficient to provide basal transcriptional activity (minimal promoter). Previous analysis of a 1.3 kb portion of the 5'-flanking region of the hβ$_3$-AR gene indicated the existence of a cAMP response element binding site, a GRE (glucocorticoid receptor response element) a CCAT box and a weak TATA box.

When constructs carrying 1.3 kb, 3 kb and 5.6 kb of the hβ$_3$-AR gene promoter using luciferase as a reporter gene were introduced into SK-N-MC cells, no transcriptional activity was apparent. Interestingly, only the construct containing the full 7 kb of the upstream flanking region was able to induce transcriptional activity. The induction of transcription, as measured by an increase in luciferase activity, was 50 fold over basal transcriptional levels (transcriptional activity of pGL3 basic). These data suggest that the region between –7 kb and –5.6 kb (Pst I-Avr II) contains strong positive regulatory elements.

Transcriptional Activity of the –7 kb to –5.6 kb of hβ$_3$-AR Promoter is Cell Specific.

Once a promoter region that regulated expression was identified, its cell specific activity was examined. The tissue and cellular distribution of the β$_3$-AR gene in man is still a matter of debate. Data from several different researchers show expression of hβ$_3$-AR primarily in BAT with little expression in WAT and other tissues. In addition, transgenic mice that carry human β$_3$-AR in mice deficient for endogenous mouse β$_3$-AR show expression only in BAT (Van Spronsen et al., supra). Since availability of human BAT is limited we examined cell specific expression using SK-N-MC cells, a human neuroblastoma cell line that expresses β$_1$ and β$_3$-ARs (Granneman et al., supra) but not β$_2$-ARs.

Constructs carrying the above described deletions (FIG. 3) were introduced into SK-N-MC cells as well as CV-1 and HeLa cells which do not express β$_3$-ARs. As noted above, the –7 hβ$_3$/Luc transfected in SK-N-MC cells exhibits about a 50-fold induction in luciferase activity. However, none of the constructs introduced in CV-1 and HeLa cells had transactivation ability. These data strongly suggest that regulatory elements present in the distal (between –7 kb and –5.6 kb) 5' flanking region bind protein(s)/factor(s) present in SK-N-MC cells to provide cell specific expression.

Regulatory Elements Present in –7 kb to –5.6 kb are Strong Activators of hβ$_3$-AR Gene Promoter in SK-N-MC Cells.

Figure 4:
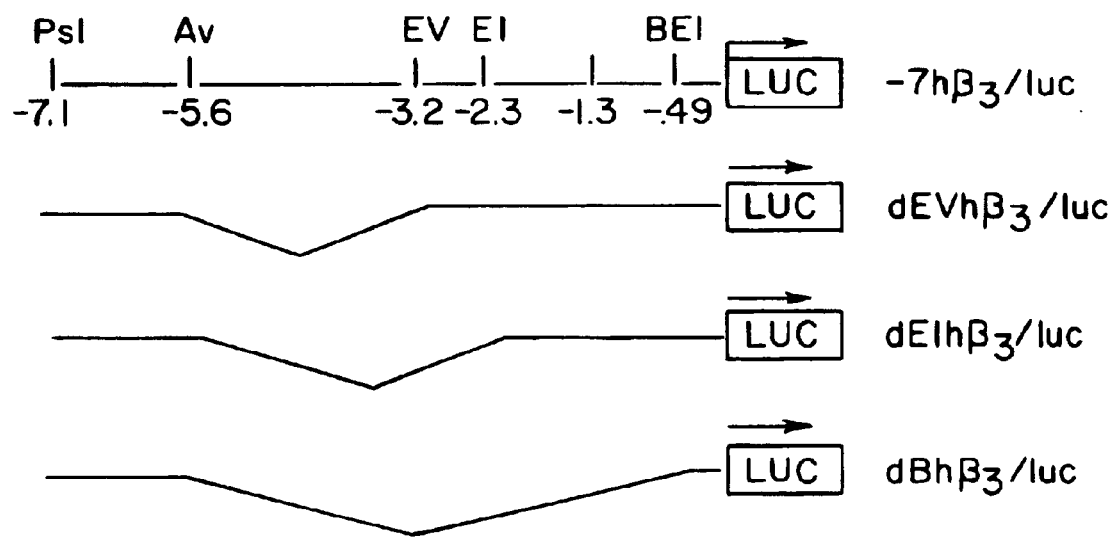
FIG. 4: Constructs to evaluate the effect of far upstream region on transcription activity. Transfection constructs were made by keeping region between –7 to –5.6 and deleting regions between AvrII and EcorV, EcoRI and BstEII to make dEVh$\beta$3AR/luc, dEIh$\beta$3AR/luc and dBh$\beta$3AR/luc respectively.

In order to investigate the importance and sufficiency of regulatory elements present in the distal region of the hβ$_3$-AR promoter, a series of DNA constructs were made, maintaining 1.5 kb of distal promoter (region between –7 to –5.6) and deleting regions between Avr II and EcoRV(dEV), EcoRI (dEI) and BstEII (dB) as shown in FIG. 4. All constructs were introduced into SK-N-MC and CV-1 cells by means of CaPO$_4$ precipitation. The constructs dEV, dEI and dB appeared to have the same activation effect on transcription as their parent construct –7hβ$_3$/Luc, suggesting that regulatory elements located within the 1.5 kb distal promoter region are responsible for maximal transcriptional activity of the hβ$_3$-AR gene promoter. No increase or decrease in the level of luciferase activity with the 3 deletion constructs when compared with –7 kbhβ$_3$/Luc was observed. Thus, these data suggested that either no additional enhancer or repressor elements exist within the sequence between –5.6 kb and –0.5 kb of the promoter that can modulate transcription of the hβ$_3$-AR gene, or that positive regulatory elements present in the promoter region between –7 kb and –5.6 kb have a dominant role in directing transcription of the hβ$_3$-ARs gene in SK-N-MC cell.

Figure 5:
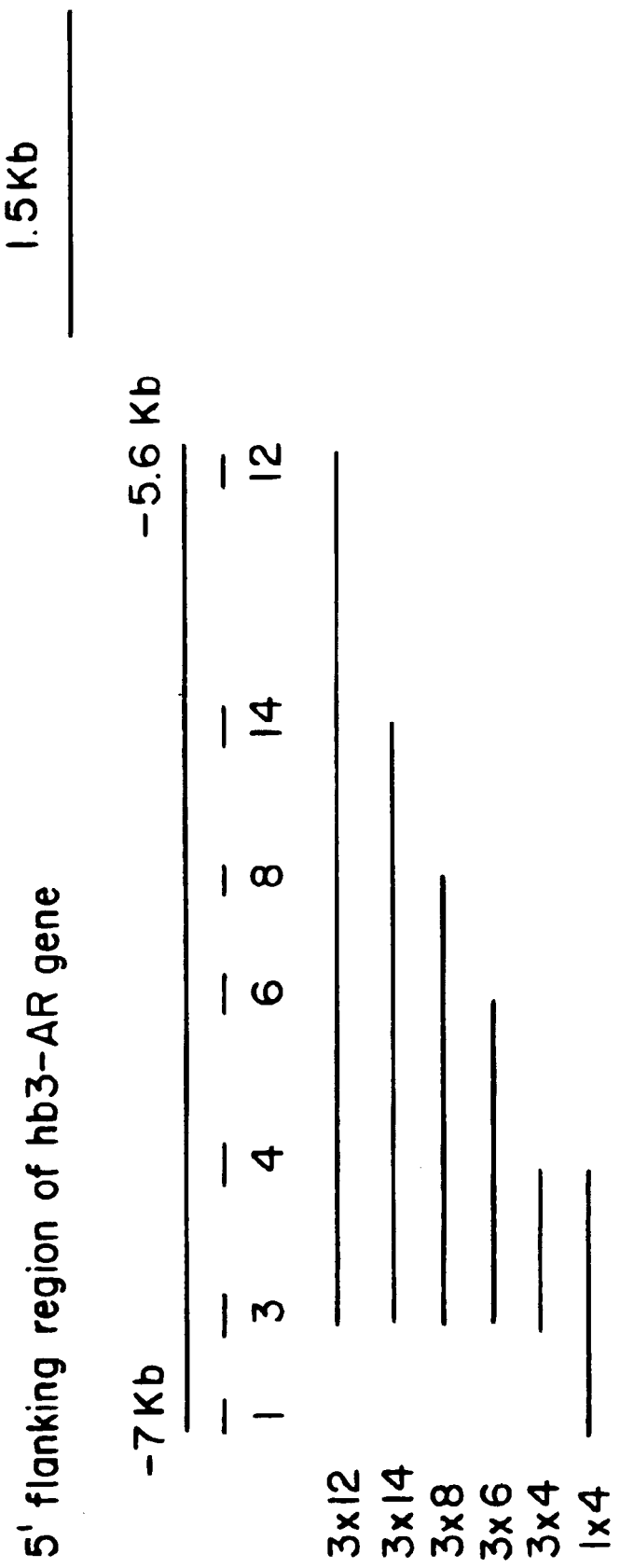
FIG. 5: Further analysis of 1.5 kb of distal promoter. A series of PCR products were made and ligated to a TK minimal promoter within pGL3 basic.

To precisely identify the location and sequence of regulatory elements within the 1.5 kb distal promoter region, a series of PCR products that covered regions between designated primers (primers are labeled with numbers) were made and ligated to a luciferase reporter gene and HSV TK minimal promoter (FIG. 5). All constructs were transiently transfected into SK-N-MC and CV-1 cells. The data from these experiments support the following conclusions: (1) The region between primers "6" and "8" (200 bp) contains regulatory elements necessary for transcriptional activity of the distal promoter region; (2) The region between primers "12" and "14" may contain elements that behave as a repressor; (3) The activities of the regions between primer numbers "3" and "12", "3" and "14" and "3" and "8" are cell specific, since no transcriptional activity was observed in transfected CV-1 cells.

The above described DNA constructs used the heterologous HSV TK promoter as a minimal promoter. In order to exclude the possibility that non-specific interactions between the TK promoter and positive regulatory elements of the hβ$_3$-AR promoter cause increased transcriptional activity, we tested the ability of the region between primers "3" and "8", referred to as "3×8" (that was shown to be necessary for transcription), to induce transcription of luciferase from −0.5 kb of the endogenous promoter as a minimal promoter and from the TK promoter. An even larger positive effect on transcription (about 2.5-fold greater) is shown when endogenous promoter rather than the TK promoter is used, thus suggesting that positive regulatory elements interact better with their endogenous promoter than with a heterologous minimal promoter. In addition, the fragments "3×12", "3×14" and "3×8" are active in reverse orientation as detected by luciferase expression, suggesting that the elements present within this 1.5 kb region of the distal promoter further fulfill the characteristics of an enhancer.

Three Sites within the hβ$_3$-AR Gene Promoter (−6.5 to −6.3) Bind Nuclear Proteins from SK-N-MC Cells.

DNA constructs that contain the region between primers "3" and "6" lose the ability to induce transcription, and the region between primers "3" and "8" has full transcriptional activity. These data indicate that the region between primers "6" and "8" contains positive regulatory elements. Further studies focused on the region between primers "6" and "8".

Figure 6B:
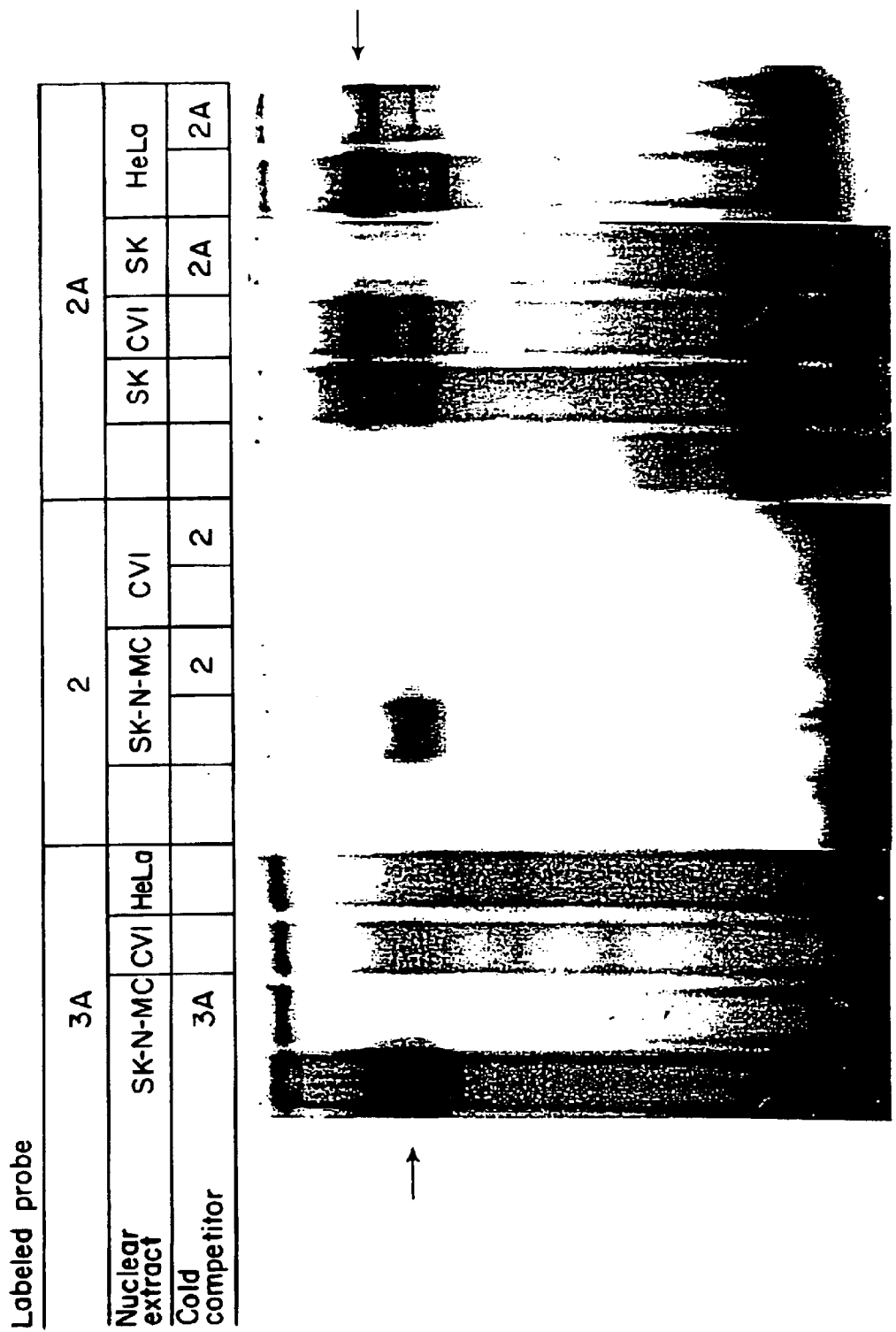
FIGS. 6A, B, C and D: EMSA experiments with oligo-nucleotides generated from sequence between –6.508 and –6.308 kp from 5' flanking region of h$\beta_3$-AR gene. A: Sequence of 200 bp between primers "6" (–6.508 kb) and "8" (–6.308 kb)(SEQ ID No:3). EMSA were done using underlined sequences as oligonucleotides, which are marked as 1, 2, 3, 4, and 1A to cover the 200 bp region, and 2A, 3A, 4A, and 1B representing overlaps between oligonucleotides 1 and 2, 2 and 3, 3 and 4, and 1A and 4, respectively. Experiments were done with doublestranded labeled oligonucleotides under the conditions described in experimental procedures. B and C: Nuclear extracts from SK-N-MC, CV-1 and HeLa cells were incubated with radiolabeled oligonucleotides described above. The Figure shows only oligonucleotides that show binding. B: Oligonucleotides 2, 2A, 3A, and C: 1B and 4A. D: Also, EMSAs were done in a presence of excess of indicated cold oligonucleotides. The amount of cold oligos was a 50× molar excess of labeled oligonucleotides unless otherwise indicated. Arrows indicate the position of major DNA-protein complexes.
Figure 6D:
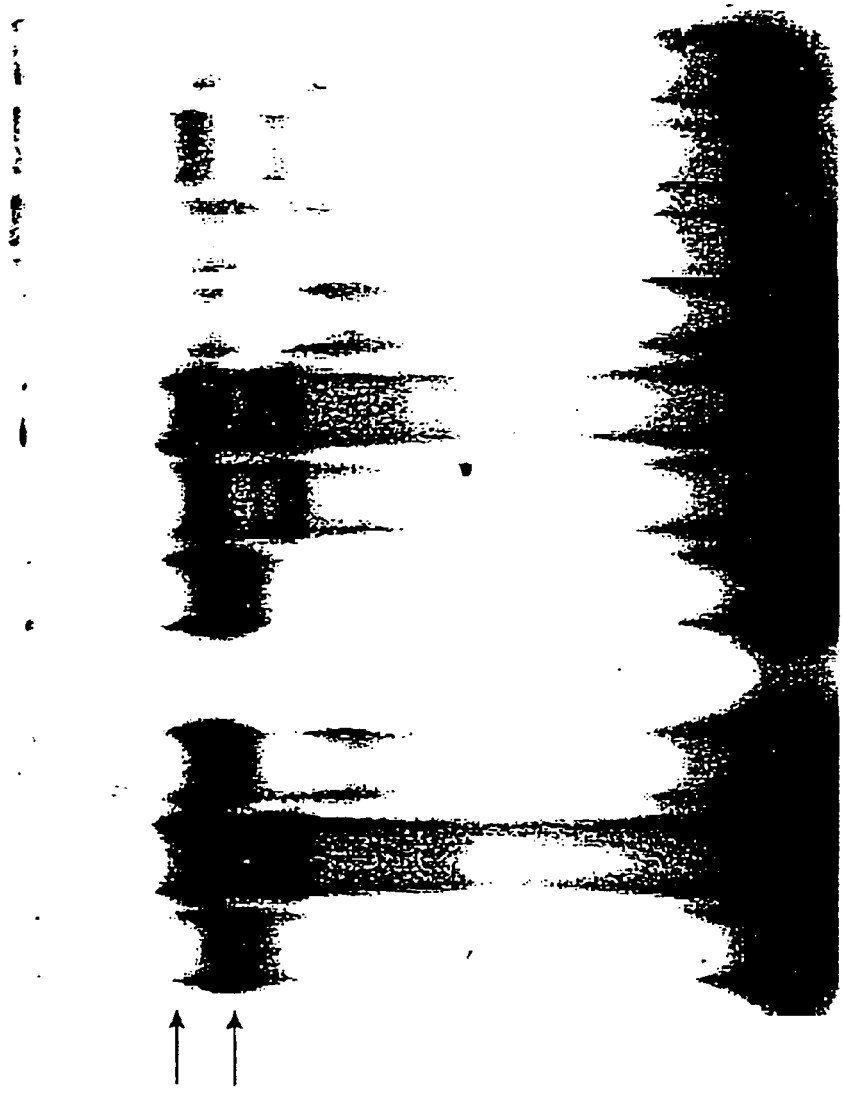

In order to further analyze the sequences that are involved in the regulation of transcription of the hβ$_3$-AR gene in SK-N-MC cells, nine double-stranded oligonucleotides 40 bp in length were constructed to cover the entire region between primers "6" and "8" of the distal promoter region, as shown in FIG. 6A. These oligonucleotides were used in EMSA with nuclear extracts from SK-N-MC cells. Oligonucleotides 2, 2A, 3A, 4A and 1B were able to bind proteins from SK-N-MC cell nuclear extracts as shown in FIGS. 6B and 6C. It is possible that oligonucleotides 2 and 3A and oligos 4A and 1B bind the same protein based on their sequence similarity as well as the mobility of bound protein. This was confirmed in competitor EMSA experiments that were performed in the presence of unlabeled oligonucleotides. Unlabeled oligonucleotide 2 was able to displace labeled oligo 3A from its protein-DNA complex (FIG. 6D) and vice versa. In addition, unlabeled oligonucleotide 1B displaced oligo 4A from its protein-DNA complex and vice versa (FIG. 6B). Oligonucleotide 2A represents the overlap between oligos 1 and 2. In EMSA with radiolabeled oligonucleotide 2A, cold oligonucleotides 1 and 2 did not displace protein from the 2A DNA/protein complex (FIG. 6D), suggesting the existence of a binding site in the overlap region.

In order to determine if these data were specific to SK-N-MC cell nuclear extracts, similar experiments were performed using nuclear extracts from HeLa and CV-1 cells. As shown in FIG. 6B, oligonucleotide 2A formed a complex with protein extracts from CV-1 and HeLa cells, thus suggesting that this segment could be involved in transcriptional regulation but was not sufficient to provide cell specific transcription of the hβ$_3$-AR. Oligonucleotides 1B and 4A bind protein from SK-N-MC and HeLa cell nuclear extracts.

Since data from transient transfection experiments showed no transcriptional activation of the hβ$_3$-AR promoter in HeLa cells, it was concluded that the protein(s) that formed a complex with 4A and 1B are important but not sufficient to provide cell specific transcription from the hβ$_3$-AR promoter. Interestingly oligonucleotide 2 binds SK-N-MC but not CV-1 and HeLa cell nuclear extract proteins (FIG. 6B). These data suggest an important role for a protein that binds the promoter sequence at position −6.46 kb (presented as oligonucleotide 2) of the hβ$_3$-AR in the regulation of hβ$_3$-AR gene transcription as well as its cell specific expression. These studies indicated that the DNA-protein complexes formed were cell line specific. For further clarity and ease of discussion, the segments represented by oligonucleotides 2A, 2(3A) and 4A(1B) are designated herein as as segments A, B and C, respectively.

Mutational Analysis of Sequences Corresponding to Segments A and B.

FIGS. 7A and 7B show mutated oligonucleotides A (overlap between 1 and 2 see FIGS. 6A) and B (overlap between oligonucleotides 2 and 3A, see FIG. 6A). These mutated oligos were used in EMSA experiments with nuclear extracts from SK-N-MC cells. These experiments were performed to identify the exact sequence responsible for the binding of nuclear extract proteins. Note that mutations were introduced within oligonucleotides in a block of 3 nucleotides, covering the whole sequence (FIGS. 7A and 7B). EMSAs were performed as described.

Oligos A1, A2, A3, A7, and A8 bound nuclear extract proteins, whereas the mutations in A4, A5, and A6 defeated binding. Thus, the core sequence in segment A necessary to bind nuclear protein is -AGGTGGGACT-(SEQ ID NO: 2), which resembles the binding site for the Sp1 binding protein.

Oligos B 1, B6, B7, and B8 bound nuclear extract proteins, whereas B2, B3, and B5 did not. Thus, mutational analysis of segment B indicated the -GCCTCTGGGGAG- sequence (SEQ ID NO: 1) as a core necessary for binding. This sequence has a 70% similarity to the binding sequence for ERF binding protein, a protein belonging to the AP-2 family of transcription factors (McPherson et al., *Proc. Natl. Acad. Sci USA*, 94, 4342–4347, 1997).

Segment C is represented by 20 repeats of a "CCTT" motif. EMSA experiments with oligonucleotides 4A and 1B that cover the 80 bp segment C show binding for nuclear extract protein from SK-N-MC and HeLa cells. It is conceivable that this 80 bp of CCTT repeats can form a tertiary structure that is recognized by nuclear extract proteins. Work from Efstratiadis (Cantor and Efstratiadis, Nucleic Acids Research 12, 8059–8072, 1984) indicates that homopurine-homopyrimidine rich segments represent sites hypersensitive to S1 nuclease. Such sites have been implicated in transcriptional regulation (Schon et al., Cell 35:837–848, 1983; Evans, and Efstratiadis, The Journal of Biological Chemistry 261:14771–14780, 1986).

The CCTT Rich Segment is Recognized by S1 Nuclease.

In order to test the hypothesis that the CCTT segment represents a hypersensitive S1 nuclease site in naked double-stranded form, an experiment as described by Evans and Efstratiadis, supra was performed. S1 nuclease sensitive sites were found between primers "6" and "8" (FIG. 3), resulting in nicking and subsequent cleavage in this region. S1 nuclease cleavage occurred in all salt concentrations, although the efficiency was lower with increased salt. These data are in agreement with data from Htun et al. (Proc. Natl. Acad. Sci. U.S.A. 81:7288–7292, 1984). Interestingly, DNA that was first digested with ScaI was not sensitive to S1 nuclease, suggesting that a structural feature relating to template superhelical density was important. Primer extension experiments using primers "6" and "16" indicated that the S1 nicking occurred within the CCTT rich segment.

Importance of Segments A, B and C for full Transcriptional Activity of the h$\beta_3$AR Gene Promoter.

To investigate the contribution and importance of each segment, a series of DNA constructs were made for transient transfection experiments where segment A and/or segment B was mutated within the sequence between −6.96 and −6.36 kb (sequence between primers "3" and "8") of the h$\beta_3$-AR gene 5'-flanking region and ligated to 0.5 kb of the endogenous minimal promoter and luciferase reporter gene. To investigate the importance of segment C, the 80 bp of CCTT repeats were deleted from the constructs, leaving sequences corresponding to segments A and B intact. In addition, constructs that carried segment A only with or without mutation (3× Awt, 3× Ac,mut) and B only with or without mutation (3× Bwt, 3× Ba,mut), were prepared. All constructs were introduced into SK-N-MC and CV-1 cells. Constructs shown to have a mutation within segments A or B lead to 50% and 60% decreases in transcriptional activity, respectively. Constructs containing mutations in both A and B show 70% lower transcriptional activity when compared to the intact "3×8" h$\beta_3$-/Luc. Region C was able to maintain 30% of luciferase activity when part of "3×8" h$\beta_3$-/Luc was transfected. However, segment C connected to the 0.5 kb endogenous minimal promoter has no transcriptional activity. Notably, neither segment A nor B were able to increase luciferase activity in the absence of segment C.

Proteins that Bind to Sequences Corresponding to Segments A and B may be Sp1 or Sp1-like Proteins.

A computer search (using the Baylor College of Medicine database; URL http:\\dot.imgen.bcm.tmc.edu:9331/seq-search/gene-search.html) of known consensus binding sites suggested the presence of known transcription factors within the −6.9 kb to −6.3 kb region of the h$\beta_3$-AR promoter. Possible Sp1 and AP-2 binding sites were indicated within sequences that corresponded to oligonucleotides 2A (segment A) and oligonucleotides 2 and 3A (segment B), respectively. To address this possibility the following experiments were undertaken:

1. EMSA using radiolabeled oligonucleotides 2A (segment A) and 2, 3A (segment B) with SK-N-MC nuclear extracts and unlabeled oligonucleotides (100-fold molar excess) identical to consensus binding sites for Sp1 and AP-2 as competitors;
2. Supershift EMSA experiments with Sp1 and AP-2 antibodies, after binding of HeLa and SK-N-MC nuclear extracts to radiolabeled Sp 1, AP-2, 2A (segment A), and 3A (segment B) oligos.

Sp1 cold oligonucleotide in 100-fold molar excess was able to displace radiolabeled oligonucleotide 2A from its complex with nuclear extract protein from SK-N-MC cells. In addition, the protein/2A DNA complex was supershifted using Sp1 antibody, in the same manner as protein/Sp1 oligonucleotides. These data suggest that the protein that binds oligonucleotide 2A is Sp1 or an Sp1 like protein.

Unlabeled AP-2 oligonucleotides, even in a 200-fold molar excess, could not displace radiolabeled oligonucleotide 3A from its complex with an SK-N-MC cell nuclear extract. In addition radiolabeled AP-2 oligonucleotide formed a complex with protein from SK-N-MC cell nuclear extracts that cannot be displaced by the presence of 100-fold molar excess of 2(3A) unlabeled oligonucleotides. Also, AP-2 antibody was able to supershift the AP-2 complex with protein from SK-N-MC and Hela cell nuclear extracts, while the 2(3A) complex with SK-N-MC cells nuclear extract was not super shifted. These results strongly suggest that transcription factors present in SK-N-MC cells that bind to the sequence within oligonucleotide 2 (segment B) represent a novel protein or proteins. Given the sequence similarity between the AP-2 consensus binding site and segment B it is conceivable that this protein(s) represents an AP-2 like protein that is expressed in SK-N-MC, but not in CV-1 and HeLa cells, and that has not yet been described.

In addition, it has been found that the protein(s) that bind segment B is sensitive to heating; heating of nuclear extract from SK-N-MC cells 10 minutes at 90° C. completely abolishes binding of proteins from nuclear extract to region "B".

Transcription Factors that Bind to Segments A and B are Present in Nuclear Extract Isolated from Brown Adipose Tissue.

$\beta_3$-ARs are expressed in BAT and WAT in rodents and BAT in man. In order to test for the presence of the above described binding proteins, nuclear extracts from mouse WAT and BAT were isolated and employed in EMSA experiments, with and without a 50-fold molar excess of cold probe. Nuclear extracts from liver, muscle, and the perirenal depot were also used for binding of radiolabeled 2A, 2, and 3A (segments A and B).

Protein (transcription factors) present in liver nuclear extract bound oligonucleotide 2A (segment A), but did not form complexes with oligonucleotide 3A (segment B). Muscle nuclear extract bound only the 2A labeled oligonucleotide. Nuclear extract from WAT showed binding for oligonucleotide 2A (segment B) but not 2 (segment A). However, nuclear extract proteins from BAT bound all labeled oligonucleotides in a sequence specific manner shown by EMSA using cold competitor. These data are in good agreement with the in vivo expression pattern of the h$\beta_3$-AR gene (Ito et al., $10^{th}$ International Congress of Endocrinology, San Francisco, poster session P1-860, Volume 1, pp. 215, 1996). In addition, nuclear extract isolated from a primary culture of human white adipose tissue (perirenal depot) provided by Zen-Bio Inc. (Research Triangle Park, NC) was tested. After seven days exposure the same pattern of binding for corresponding labeled oligonucleotides was obtained that had been seen previously with nuclear extracts from SK-N-MC cells and BAT.

Perirenal depots in rodents are the second largest depot of brown fat. Primary adipocyte cultures developed from the human perirenal depot show the morphological appearance of mitochondria as well as multilocular lipid droplets and genetic characteristics (expression of UCP-1 and $\beta_3$-AR) of BAT (Champigny and Ricquier, Journal of Lipid Research 37:1907–1914, 1996). Thus, it is likely that the protein(s) from the perirenal depot preparation that form complexes with radiolabeled probes come from cells with a BAT phenotype rather than from white adipocytes. The number of cells with a BAT phenotype is probably small, since a signal was observed only after 10 days of exposure compared with the relatively short (8–10 hour) exposure needed when using SK-N-MC cell nuclear extracts.

Discussion

In rodents, $\beta_3$-AR is abundantly expressed in both white and brown adipose tissue, with low levels in gallbladder and small intestine. The importance of this receptor and its expression in rodent BAT and WAT, two tissues that play a major role in the regulation of overall energy balance, is further emphasized by data showing dramatic weight loss and glycemic improvement in rodent models of obesity with treatment with $\beta_3$-AR specific agonists (Carroll et al., Diabetes 34:1198–1204, 1984; Umekawa et al., European Journal of Endo. 136:429–437, 1997; Yoshida et al.; J. Nutr. Sci. Vitaminol. (Tokyo) 36:75–80, 1990; Yoshida et al., Endocrinol. Japon 38:397–403, 1991; Smith et al., New Antidiabetic Drugs, Ed., Bailey, C. J., and Flatt, P. R., London, 1990; Largis et al., Drug Dev. Res. 32:69–76, 1994; Bloom et al., Journal of Medicinal Chemistry 35:3081–3084, 1992; Cawthorne et al., American Journal of Clinical Nutrition 55:252S–257S, 1992). The physiologic importance as well as tissue distribution of $\beta_3$ receptors in humans has been more controversial.

Using sensitive techniques, among them Northern blots, RNase protection assays as well as RT-PCR (reverse transcriptase PCR), several groups of investigators were able to detect message for $\beta_3$-ARs in humans (Krief et al., J. Clin. Invest. 91:344–349, 1993; Thomas et al., Mol. Pharmacol. 43:343–348, 1993). These studies demonstrated that mRNA for $\beta_3$-ARs is expressed in brown and white adipose tissue isolated from different fat depots and that the level of expression of h$\beta_3$-AR in WAT varies depending on the fat depot that is examined and the sensitivity of the method utilized (Strosberg, Annu. Rev. Pharmacol. Toxicol. 37:421–450, 1997). Low levels of $\beta_3$-AR mRNA expression were also detected in gall bladder, small intestine, stomach and prostate, but no $\beta_3$-AR mRNA has been detected in brain tissues (Strosberg, Annu. Rev. Pharmacol. Toxicol., 37:421–450, 1997).

Lack of abundant expression of this receptor in key tissues such as BAT and WAT, as well as a low level of BAT in man, may explain, at least in part, the poor clinical performance of previously tested $\beta_3$ agonists for treating obesity. A better understanding of h$\beta_3$-AR regulation could lead to improved efficiency of these agents by providing a means of enhancing receptor expression. In order to better understand factors and mechanisms that regulate expression level of h$\beta_3$-ARs, experiments were designed to identify cis-regulatory elements within the h$\beta_3$-AR promoter, and their corresponding trans-acting factors. Since a human BAT cell line was not available, h$\beta_3$-AR receptor expression was studied in SK-N-MC cells, a human neuroblastoma cell line that expresses $\beta_3$-AR endogenously.

Using 5' RACE, we first confirmed that the h$\beta_3$-AR gene uses multiple transcription start sites. The utilization of multiple cap sites has been previously described in the case of the $\beta_3$-AR gene (Kobilka et al., The Journal of Biological Chemistry 262:7321–7327, 1987) and $\alpha_{1b}$-AR genes (Ramarao et al., The Journal of Biological Chemistry 267:21936–21945, 1992). Our results from the 5' RACE experiments are in good agreement with data previously reported by Granneman and Lahners (Endocrinology, 135:1025, 1994) using a nuclease protection assay on mRNA from SK-N-MC cells and human brown adipose tissue and by Van Spronsen et al. (Eur. J. Biochem., 273:1117, 1993) using an S1 nuclease assay and primer extension on mRNA from human perirenal and omental adipose tissues.

Next, the minimum $\beta_3$-AR promoter was evaluated. Using a luciferase gene linked to the 5'-flanking region of the h$\beta_3$-AR as a reporter gene, segments of the 5'-flanking region necessary for the induction of luciferase activity were identified. Data from these experiments suggested that a promoter region 500 bp upstream from the translation start site is sufficient to provide minimal transcription. Five hundred bp of proximal h$\beta_3$-AR gene promoter provided a 5–6 fold increase in luciferase activity when compared to pGL3 basic levels of transcription. Activation of transcription by this promoter region is observed in SK-N-MC cells (cells that endogenously express $\beta_3$-ARs) as well as CV-1 and HeLa cells. Thus, these data suggest that regulatory elements located within this 500 bp region upstream from the translation start site may define the minimal promoter.

Recently, transgenic animals were made containing the h$\beta_3$-AR gene introduced into endogenous $\beta_3$-AR knock-out mice (Ito et al., $10^{th}$ International Congress of Endocrinology, poster session $\beta$1–860, Vol. 1, pp. 215, San Francisco, Calif., 1996). In these animals the presence of a 500 bp region upstream of the translation start site of the h$\beta_3$-AR gene promoter was sufficient to induce expression of the transgene in a tissue specific manner (expression only in BAT). These findings are in good agreement with our data showing that a similar region of the promotor was sufficient to cause basal expression levels in SK-N-MC cells, indicating that the mechanisms and transcription factors involved in the basal transcriptional regulation of $\beta_3$-ARs in human and mouse BAT are the same as those in SK-N-MC cells. However, identification of the minimum promoter 500 bp 5' to the $\beta_3$-AR start site does not indicate whether there is an enhancer, much less where any such enhancer might be located or what its characteristics may be.

Careful examination of the sequence of the h$\beta_3$-AR promoter for the presence of TATA, CCAAT and GC boxes revealed the existence of two TATA-like sequences that are significantly different from the described consensus sequences for a TATA box (Bucher, J. Mol. Biol. 212:563–578, 1990). In addition, there are no GC-boxes in the proper orientation to the TATA box like sequences, often a characteristic of gene promoters that have a weak TATA box (Bucher, supra). However, the presence of CCAAT sequences, cap sites and a weak TATA-box can still provide recognition and initiation sites for RNA polymerase II (Smale et al, Cell 57:103–113, 1989). Alternatively, the weak h$\beta_3$-AR gene promoter organization may indicate the presence of strong upstream regulatory elements that are responsible for full transcriptional activity. The presence of weak promoter elements has been previously described for a number of genes in addition to other members of the adrenergic receptor family such as the $\alpha_{1b}$-AR (Razik et al., J. Biol. Chem., 272:28237–28246, 1997) and $\alpha_{1a}$-AR genes (Ramarao, The Journal of Biological Chemistry, 267:21936–21945, 1992). The $\alpha_{1b}$-AR gene has CCAAT and Sp1 binding sites, but a very weak TATA box. On the other hand, the promoter of the $\alpha_{1a}$-AR gene has no CAAT or TATA box elements but possesses several GC-regions that correspond to an Sp1 binding site. Sequence analysis of the h$\beta_3$-AR gene promoter, specifically the 1.3 kb region upstream of the translation start site, reveals the existence of four CREBP consensus binding sites indicating cAMP as a potential regulator of h$\beta_3$-AR transcription. In addition, glucocorticoid receptor (GRE), AP-1 and NF-1 binding sites are also present. However, none of these response elements and transcription factors are sufficient to explain the cell specific (BAT and SK-N-MC) expression of h$\beta_3$-ARs.

Deletion analysis of the 5' flanking region from the $\beta_3$-AR gene has established that the region between −7 kb and −5.6 kb of the distal promoter directs strong expression in SK-N-MC cells. The DNA construct −7h$\beta_3$/Luc induced a 50 to 70 fold increase in luciferase activity over basal levels. Constructs that contained 1.3 kb, 3 kb or 5.6 kb of the promoter sequence but not the −5.6 to −7 kb region did not show any luciferase activity (FIGS. 3A and 3B), suggesting the presence of a strong positive regulatory element(s) within the −7 kb to −5.6 kb region. Indeed, regulatory elements present in the 1.5 kb (between −7 kb and −5.6 kb) region of the distal promoter appear sufficient to provide full transcriptional activity since vectors that contain deletions as large as the region between −5.6 to 0.5 kb are still able to induce luciferase activity to the level seen with the full −7h$\beta_3$/Luc construct (FIG. 4B). The −7h$\beta_3$/Luc as well as constructs with various deletions between −5.6 and 0.5 kb that still contain the DNA sequence between −7 kb and −5.6 kb, exert a positive effect on transcriptional activity in a cell specific manner. Specifically, increased luciferase activity was observed only in transiently transfected SK-N-MC, but not in CV-1 or HeLa cells. These data indicate the existence of strong positive and cell specific positive cis-regulatory element(s) within this 1.5 kb portion of the distal h$\beta_3$-AR gene promoter.

Further dissection of the sequence between −7 kb and −5.6 kb has localized the enhancer elements to a 200 bp region between positions −6.50 kb and −6.30 kb (designated as the region between primers "6" and "8" "6×8") (FIG. 5). The presence of these regulatory elements is necessary and sufficient to drive the transcription of a luciferase reporter gene using a TK promoter as well as a −0.5 kb region of the endogenous promoter. The fact that these elements can stimulate transcription from both endogenous and heterologous promoters, and in either orientation, suggest characteristics of a typical enhancer. The activity of these h$\beta_3$-AR positive regulatory elements is cell type specific since transcriptional activation was observed only in SK-N-MC, but not CV-1 cells.

The EMSA experiments with oligonucleotides that span 200 bp of the putative regulatory region identified 3 sequences that bind nuclear extract proteins: segment A-ggtgtaGGTGGGactcgtga (SEQ ID NO: 30), segment B—GCCTCTCTGGGGAGCAGCTTCTCC (SEQ ID NO: 31) (FIGS. 6A and 7), and segment C, a segment composed of 20 repeats of a CCTT motif.

Segment A binds proteins present in nuclear extracts from SK-N-MC, CV-1, and HeLa cell lines indicating that this protein(s)/DNA complex(es) does not provide cell specific expression of the h$\beta_3$-ARs. From the EMSA data it appears that oligonucleotide A binds a complex of two proteins. One is identified as an Sp1 like protein.

Mutational analysis of segment A indicated that a -aGGTGGGact-(SEQ ID NO: 2) sequence is responsible for the binding of transcription factor(s). This core sequence is similar to the consensus binding site for the Sp1—transcription factor (taGGCGgggc-; SEQ ID NO: 32). Indeed, both EMSA experiments with the consensus binding site for the Sp1 protein as a competitor and the supershift using Sp1 antibody, show that this protein is Sp1 or a very closely related Sp1-like protein. The Sp1 binding protein belongs to a family of zinc-finger transcription factors that can activate transcription itself, but very often play an important role in transcription as a co-regulator with other transcription factors. The Sp1 binding site is located in the proximal region of promoters of numerous genes (Bucher, J. Mol. Biol., 212:563–578, 1990) and is usually involved in the linking of distal control elements. Although the presence of a Sp1 binding site cannot explain cell and tissue specific transcriptional regulation, its corresponding binding protein plays a very important role in the transcription of numerous genes (Razik et al., J. Biol. Chem., 272:28237–28246, 1997; Cohen, et al., The American Society for Biochemistry and Molecular Biology, Inc. 272:2901–2913, 1997; Viñals et al., The Journal of Biological Chemistry 272:12913–12921, 1997; Dawson et al., The Journal of Biological Chemistry 263:3372–3379, 1988; Rolland et al., The Journal of Biological Chemistry 271:21297–21302, 1996). In the h$\beta_3$-AR gene promoter, the Sp1-like protein binding site is located 6.47 kb upstream from the translation start site, and may indicate the presence of an additional exon far upstream from the designated translation start site. The presence of a novel exon is highly unlikely since our 5' RACE experiments as well as extensive Southern blot analysis confirmed the genetic structure of the 5' end of the h$\beta_3$-AR gene.

The protein that binds segment B is expressed in nuclear extracts from SK-N-MC but not from CV-1 or HeLa cells, suggesting that it may play an important role in cell specific expression of the receptor. Mutational analysis of B revealed the sequence -GCCTCTGGGGAG-(SEQ ID NO: 1) as a core responsible for binding SK-N-MC nuclear extract protein. The sequence shows some similarity to the AP-2 consensus binding site. However, in EMSA experiments using either AP-2 oligonucleotide as a competitor or AP-2 antibody for supershift, oligonucleotide 2(3A) could not be displaced from the DNA/protein complex, nor was there supershift of that protein with antibody. Nevertheless, segment B has a 78% similarity with the ERF consensus binding site that belongs to a family of AP-2 transcription factors (McPherson et al., Proc. Natl. Acad. Sci. USA, 94:4342–4347, 1997). Thus, segment B represents a binding site for a novel transcription factor present in SK-N-MC cells, possibly for a novel AP-2 protein.

On the 3' end of the h$\beta_3$-AR gene enhancer, an 80 bp sequence (segment C) that represents 20 repeats of a CCTT motif was identified. It is obvious from EMSA data that segment C serves as a binding site for nuclear extract proteins, even though it seems to lack the usual sequence complexity of sequence specific DNA binding sites. This homopyrimidine rich sequence resembles a motif recognized as an S1 nuclease hypersensitive site (Cantor et al., Nucleic Acids Research, 12:8059–8072, 1984). In experiments where the 200 bp regulatory region was treated with S1 nuclease digestion, S1 nuclease recognized this region and caused nicking within it. Based on data from sequencing and primer extension, all the nicking and cleavages occurred within the CCTT region. In naked DNA templates these regions are thought to present single-stranded regions, perhaps due to a strand sliding mechanism. In vivo, the site recognized by S1 nuclease is usually indicated as a hypersensitive site where the organization of chromatin facilitates binding of transcription factors. Various factors identified in the SK-N-MC extract may bind the poly CCTT segment by sequence or structural determinants, or both. Presence of such a motif (characterized by CCTT repeats) further confirmed the importance of region C in transcriptional regulation of the h$\beta_3$-AR gene.

The importance and relative contribution of binding sites A, B and C to the full transcriptional activity of the h$\beta_3$-AR promoter was examined. Luciferase activity was decreased 50% and 60% when mutations within A or B are introduced, respectively. A 70% decrease in transcriptional activity was observed when both sites were mutated. Region C was able to maintain low level luciferase activity probably interacting with regulatory elements present within the minimal promoter and/or the region upstream of A. However, individually segments A, B, and C did not activate transcription. Full transcriptional activity of positive regulatory elements within the h$\beta_3$-AR promoter require the presence of intact regions A, B and C. The close localization of three cis-acting elements (regions A, B, and C) implies interaction between the trans-acting factors bound to these regions and suggests that all three factors are required for full enhancer activity. Indeed, the data indicate that the trans-acting factors act synergistically to achieve full activity of enhancer. Synergism between contiguous transcription factors is well recognized. Data from numerous gene transcription experiments emphasize the importance of the spacial and temporal arrangement of multiple transcription factors at an enhancer element to drive tissue-specific and differentiation-dependent expression (Yamamato et al., *Transcriptional Regulation*, Cold Spring Harbor Laboratory Press, 1992, pp. 1169–1192).

The $\beta_3$-ARs are abundantly expressed in rodent BAT and WAT. However data from several groups have shown only limited, if any, expression of human $\beta_3$-ARs in WAT, along with robust expression in BAT. In order to confirm and extend these findings, nuclear extract proteins from mouse BAT, WAT, muscle, and liver, and differentiated human white adipocytes isolated from the perirenal depot, were tested for the presence of identified trans-acting factors. The same pattern of binding in nuclear extracts from mouse BAT and human white adipocyte cells isolated from the perirenal depot as had been seen with SK-N-MC nuclear extracts was observed. This was true for both A and B regulatory regions. Nuclear extract isolated from mouse epididymal fat depots did not show any binding of regions B or C, and only weak binding for region A. The perirenal depot, as shown by many laboratories (Champigny et al., Journal of Lipid Research, 37:1907–1914, 1996; Kortelainen et al., J. Histochem. Cytochem., 41:759–764, 1993; Lean et al., International Journal of Obesity 10:219–227, 1986), contains cells that express uncoupling protein 1 (UCP-1). UCP-1 expression is unique to BAT cells and verifies the presence of brown adipocytes in this depot. Therefore, it is possible that the presence of trans-acting factors in nuclear extracts from the human perirenal fat depot comes from their expression in brown adipocytes. It is conceivable that these factors exist in WAT at a level too low to be detected by the methods used here. However, even after the film was exposed for 10 days, no signal was observed. On the other hand, nuclear extracts from liver and WAT showed binding of oligonucleotide 2A (FIG. 6A), which hybridizes to Segment A, a region shown previously to bind an Sp-like protein. In muscle, with two different preparation(s), binding of 2A (segment A-specific) oligonucleotide was observed, but not for (3A) (segment B-specific) or 4A (1B) (segment C-specific) (FIG. 6A). If proteins that bind oligonucleotide 2 (segment B) provide tissue specific expression, then data from EMSA experiments that show a lack of binding of muscle and liver nuclear extracts with oligonucleotide 2 are in agreement with the tissue specific expression pattern of the $\beta_3$-ARs, since the receptor is not expressed in these tissues.

A better understanding of $\beta_3$-AR transcription can lead to pharmacological intervention targeted to selectively increase $\beta_3$-AR expression and thus enhance the effectiveness of noradrenalin, an endogenous ligand, as well as pharmacologic agents that are $\beta_3$ selective agonists. Transcriptional modulations that increase expression of $\beta_3$-AR and its enhanced activity should cause a sustained increase in resting metabolic rate, energy expenditures and weight loss. In addition, identification of these cis- and trans-activities that direct transcription of h$\beta_3$-AR in SK-N-MC cells and BAT may shed light on mechanisms and factors that are responsible for white and brown adipose tissue development.

In summary, regulatory elements responsible for transcriptional regulation of the h$\beta_3$-AR in SK-N-MC cells were identified and localized between –6.50 and –6.30 kb of the proximal promoter. All three segments within cis-acting elements act synergistically to achieve full transcriptional activity. One of the segments, labeled as segment B, represents a binding site for a trans-acting factor present only in SK-N-MC cells and BAT, but not detectable in CV-1 and HeLa cells, or in mouse liver, muscle and WAT cells.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Patents, patent applications, and publications are cited throughout this application, the disclosures of which are incorporated herein by reference in their entireties.

What is claimed is:

1. A method of screening for a compound that increases activity of a human Sp1 or B segment-binding $\beta_3$-adrenergic receptor ($\beta_3$-AR) trans-activating factor in mammalian cells, which method comprises:
   (a) contacting mammalian cells capable of producing the Sp1 or B segment-binding $\beta_3$-AR trans-activating factor with a test compound; and
   (b) detecting an increase in a level of activity of the Sp1 or B segment-binding $\beta_3$-AR trans-activating factor, wherein the increase in the level of activity of the Sp1 or B segment-binding $\beta_3$-AR trans-activating factor results in an increase in the level of $\beta_3$-AR gene product relative to a level of expression prior to contact with the test compound.

2. A method of screening for a compound that increases activity of a human $\beta_3$-adrenergic receptor ($\beta_3$-AR) trans-activating factor in mammalian cells, which method comprises:
   (a) contacting mammalian cells capable of producing the $\beta_3$-AR trans-activating factor with a test compound; and
   (b) detecting an increase in a level of activity of the $\beta_3$-AR trans-activating factor, wherein the increase in the level of activity of the $\beta_3$-AR trans-activating factor is detected by detecting an increase in the level of expression of a reporter gene operatively associated with an isolated nucleic acid having a nucleotide sequence GCCTCTGGGGAG (SEQ ID NO:1) relative to a level of expression prior to contact with the test compound.

3. A method according to claim 1, wherein the increase in the level of activity of the $\beta_3$-AR trans-activating factor is detected by detecting an increase in the amount of $\beta_3$-AR trans-activating factor present in the cells after contacting them with the test compound relative to the amount present prior to contact with the test compound.

4. A method according to claim 1, wherein the cells do not endogenously express $\beta_3$-AR.

5. A method according to claim 4, wherein the cells are selected from the group consisting of HeLa cells, CV-1 cells, and WAT cells.

6. A method of screening for a compound that inhibits activity of a human Sp1 or B segment-binding $\beta_3$-adrenergic receptor ($\beta_3$-AR) trans-activating factor in mammalian cells, which method comprises:
   (a) contacting mammalian cells capable of producing the Sp1 or B segment-binding $\beta_3$-AR trans-activating factor with a test compound; and
   (b) detecting a decrease in a level of activity of the Sp1 or B segment-binding $\beta_3$-AR trans-activating factor, wherein the decrease in the level of activity of the Sp1 or B segment-binding $\beta_3$-AR trans-activating factor results in a decrease in the level of $\beta_3$-AR gene product relative to a level of expression prior to contact with the test compound.

7. A method of screening for a compound that inhibits activity of a human $\beta_3$-adrenergic receptor ($\beta_3$-AR) trans-activating factor in ammalian cells, which method comprises:
   (a) contacting mammalian cells capable of producing the $\beta_3$-AR trans-activating factor with a test compound; and
   (b) detecting a decrease in a level of activity of the $\beta_3$-AR trans-activating factor, wherein the decrease in the level of activity of the $\beta_3$-AR trans-activating factor is detected by detecting a decrease in the level of expression of a reporter gene operatively associated with an isolated nucleic acid having a nucleotide sequence GCCTCTGGGGAG (SEQ ID NO:1) relative to a level of expression prior to contact with the test compound.

8. A method according to claim 6, wherein the decrease in the level of activity of the $\beta_3$-AR trans-activating factor is detected by detecting a decrease in the amount of $\beta_3$-AR trans-activating factor present in the cells after contacting them with the test compound relative to the amount present prior to contact with the test compound.

9. A method according to claim 6, wherein the cells endogenously express β$_3$-AR.

10. A method according to claim 9, wherein the cells are selected from the group consisting of neuroblastoma and BAT cells.

11. A method of screening for a compound that increases activity of a human β$_3$-adrenergic receptor (β$_3$-AR) trans-activating factor in mammalian cells, which method comprises:
- (a) contacting mammalian cells capable of producing the β$_3$-AR trans-activating factor with a test compound; and
- (b) detecting an increase in a level of activity of the β$_3$-AR trans-activating factor, wherein the level of activity of the β$_3$-AR trans-activating factor is detected by an increase in the level of expression of a reporter gene operatively associated with an isolated nucleic acid selected from the group consisting of:
  - (i) about a 7 kb genomic DNA 5' flanking region of a β$_3$-AR transcription start site,
  - (ii) a deletion construct of a 7 kb genomic DNA located upstream of a β$_3$-AR transcription start site;
  - (iii) a nucleic acid comprising a nucleotide sequence that is greater than 80% identical to the nucleotide sequence GCCTCTGGGGAG (SEQ ID NO:1) located 5' to an Sp-1 binding site relative to a transcription start site; and
  - (iv) a nucleic acid comprising a heterologous coding sequence operatively associated with a promoter and operatively associated with a nucleotide sequence that is greater than 80% identical to the nucleotide sequence GCCTCTGGGGAG (SEQ ID NO:1) in proximity to an Sp-1 binding site, whereby expression of the heterologous protein is regulated in a tissue specific manner.

12. A method of screening for a compound that decreases activity of a human β$_3$-adrenergic receptor (β$_3$-AR) trans-activating factor in mammalian cells, which method comprises:
- (a) contacting mammalian cells capable of producing the β$_3$-AR trans-activating factor with a test compound; and
- (b) detecting a decrease in a level of activity of the β$_3$-AR trans-activating factor, wherein the level of activity of the β$_3$-AR trans-activating factor is detected by a decrease in the level of expression of a reporter gene operatively associated with an isolated nucleic acid selected from the group consisting of:
  - (i) about a 7 kb genomic DNA 5' flanking region of a β$_3$-AR transcription start site,
  - (ii) a deletion construct of a 7 kb genomic DNA located upstream of a β$_3$-AR transcription start site;
  - (iii) a nucleic acid comprising a nucleotide sequence that is greater than 80% identical to the nucleotide sequence GCCTCTGGGGAG (SEQ ID NO:1) located 5' to an Sp-1 binding site relative to a transcription start site; and
  - (iv) a nucleic acid comprising a heterologous coding sequence operatively associated with a promoter and operatively associated with a nucleotide sequence that is greater than 80% identical to the nucleotide sequence GCCTCTGGGGAG (SEQ ID NO:1) in proximity to an Sp-1 binding site, whereby expression of the heterologous protein is regulated in a tissue specific manner.

* * * * *

SEQUENCE LISTING

<160> NUMBER OF SEQ ID NOS: 49

<210> SEQ ID NO 1
<211> LENGTH: 12
<212> TYPE: DNA
<213> ORGANISM: Artificial Sequence
<220> FEATURE:
<223> OTHER INFORMATION: Oligonucleotide

<400> SEQUENCE: 1
gcctctgggg ag        12

<210> SEQ ID NO 2
<211> LENGTH: 10
<212> TYPE: DNA
<213> ORGANISM: Artificial Sequence
<220> FEATURE:
<223> OTHER INFORMATION: Oligonucleotide

```
<400> SEQUENCE: 2
aggtgggact                                                             10

<210> SEQ ID NO 3
<211> LENGTH: 200
<212> TYPE: DNA
<213> ORGANISM: Homo sapien
<220> FEATURE:

<400> SEQUENCE: 3
cctggaagga agcctaagca tttgggcctg ggttgtaggt gggactcgtg acctctccca      60
gcctctgggg agcagcttct ccaatagtca ggggtctcaa tgaccttcct tccttccttc     120
cttccttcct tccttcctto cttccttcct tccttccttc cttcctttct tccttccttc     180
cttcgtgcca cttgcaaaag                                                 200

<210> SEQ ID NO 4
<211> LENGTH: 9
<212> TYPE: DNA
<213> ORGANISM: Artificial Sequence
<220> FEATURE:
<223> OTHER INFORMATION: Consensus binding site from viral and cellular
      promoters, where nucleotide 4, 5 and 6 can be A, T, C or G

<400> SEQUENCE: 4 gccnnnggc                                                              9

<210> SEQ ID NO 5
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 5
ctttccctac cgccccacgc gcgatc                                           26

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 6
gtggcgccca acggccagtg gccagtc                                          27

<210> SEQ ID NO 7
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 7
ttggcgctga ctggccactg gccgttg                                          27

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 8
```
gcgcgtagac gaagagcatc acgag                25

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 9
ctcgtgatgc tcttcgtcts cgcgc                25

<210> SEQ ID NO 10
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 10
gtgaaggtgc ccatgatgag acccaagg             28

<210> SEQ ID NO 11
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 11
ccctgtgcac cttgggtctc atcatgg              27

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 12
cctctgcccc ggttacctac cc                   22

<210> SEQ ID NO 13
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 13
actcactata gggctcgagc ggc                  23

<210> SEQ ID NO 14
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 14
ggcagcccac tggtgttggc ggtat                25

<210> SEQ ID NO 15
<211> LENGTH: 26
<212> TYPE: DNA

```
<213> ORGANISM: Artificial Sequence
<220> FEATURE:
<223> OTHER INFORMATION: Oligonucleotide primer

<400> SEQUENCE: 15
ggtacctcta ggtggaaagg tgcatg                                              26

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 16
aagcttagtc ccctccctgt cgt                                                 23

<210> SEQ ID NO 17
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 17
ctgcaggggt tgagaac                                                        17

<210> SEQ ID NO 18
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 18
gctagcgcaa gtgcaatcta taacacaggg g                                        31

<210> SEQ ID NO 19
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 19
gtcgacgctg ggattacagg tccgtgc                                             27

<210> SEQ ID NO 20
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 20
gtcgacatgc ttaggcttcc ttccagg                                             27

<210> SEQ ID NO 21
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 21
gtcgaccttt tgcaagtggc acgaagg                                             27
```

<210> SEQ ID NO 22
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 22
gtcgacacct gccagtctgc cttctc                                    26

<210> SEQ ID NO 23
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 23 gtcgaccta ggtggcagag cgagactct                                  29

<210> SEQ ID NO 24
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 24
ggtaccgcaa gtgcaatcta taacacaggg g                              31

<210> SEQ ID NO 25
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 25
ggttaccctt ttgcaagtgg cacgaagg                                  28

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 26
gttgttcctg ggactcgtga                                           20

<210> SEQ ID NO 27
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 27
tgggactcgt gacctctccc agccagacgg gagc                           34

<210> SEQ ID NO 28
<211> LENGTH: 21
<212> TYPE: DNA
<213> ORGANISM: Artificial Sequence
<220> FEATURE:

<223> OTHER INFORMATION: Oligonucleotide primer

<400> SEQUENCE: 28
cctggaagga agcctaagca t                                              21

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 29
ggcactgcta ggaacacact c                                              21

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide

<400> SEQUENCE: 30
ggtgtaggtg ggactcgtga                                                20

<210> SEQ ID NO 31
<211> LENGTH: 24
<212> TYPE: DNA
<213> ORGANISM: Artificial Sequence
<220> FEATURE:
<223> OTHER INFORMATION: Oligonucleotide

<400> SEQUENCE: 31
gcctctctgg ggagcagctt ctcc                                           24

<210> SEQ ID NO 32
<211> LENGTH: 10
<212> TYPE: DNA
<213> ORGANISM: Artificial Sequence
<220> FEATURE:
<223> OTHER INFORMATION: Oligonucleotide

<400> SEQUENCE: 32
taggcggggc                                                           10

<210> SEQ ID NO 33
<211> LENGTH: 27
<212> TYPE: DNA
<213> ORGANISM: Artificial Sequence
<220> FEATURE:
<223> OTHER INFORMATION: Oligonucleotide

<400> SEQUENCE: 33
gatccggttg taggtgggac tcgtgaa                                        27

<210> SEQ ID NO 34
<211> LENGTH: 27
<212> TYPE: DNA
<213> ORGANISM: Artificial Sequence
<220> FEATURE:
<223> OTHER INFORMATION: Oligonucleotide

<400> SEQUENCE: 34
gatccctatg taggtgggac tcgtgaa                                        27

```
<210> SEQ ID NO 35
<211> LENGTH: 27
<212> TYPE: DNA
<213> ORGANISM: Artificial Sequence
<220> FEATURE:
<223> OTHER INFORMATION: Oligonucleotide

<400> SEQUENCE: 35
gatccggtac aaggtgggac tcgtgaa                                      27

<210> SEQ ID NO 36
<211> LENGTH: 27
<212> TYPE: DNA
<213> ORGANISM: Artificial Sequence
<220> FEATURE:
<223> OTHER INFORMATION: Oligonucleotide

<400> SEQUENCE: 36
gatccggttg ttcctgggac tcgtgaa                                      27

<210> SEQ ID NO 37
<211> LENGTH: 27
<212> TYPE: DNA
<213> ORGANISM: Artificial Sequence
<220> FEATURE:
<223> OTHER INFORMATION: Oligonucleotide

<400> SEQUENCE: 37
gatccggttg taggaccgac tcgtgaa                                      27

<210> SEQ ID NO 38
<211> LENGTH: 27
<212> TYPE: DNA
<213> ORGANISM: Artificial Sequence
<220> FEATURE:
<223> OTHER INFORMATION: Oligonucleotide

<400> SEQUENCE: 38
gatccggttg taggtggctg tcgtgaa                                      27

<210> SEQ ID NO 39
<211> LENGTH: 27
<212> TYPE: DNA
<213> ORGANISM: Artificial Sequence
<220> FEATURE:
<223> OTHER INFORMATION: Oligonucleotide

<400> SEQUENCE: 39
gatccggttg taggtgggac agctgaa                                      27

<210> SEQ ID NO 40
<211> LENGTH: 27
<212> TYPE: DNA
<213> ORGANISM: Artificial Sequence
<220> FEATURE:
<223> OTHER INFORMATION: Oligonucleotide

<400> SEQUENCE: 40
gatccggttg taggtgggac tcgacta                                      27

<210> SEQ ID NO 41
<211> LENGTH: 28
<212> TYPE: DNA
<213> ORGANISM: Artificial Sequence
<220> FEATURE:
<223> OTHER INFORMATION: Oligonucleotide
```

<400> SEQUENCE: 41
gatccgcctc tgggagcag cttctcca                                              28

<210> SEQ ID NO 42
<211> LENGTH: 28
<212> TYPE: DNA
<213> ORGANISM: Artificial Sequence
<220> FEATURE:
<223> OTHER INFORMATION: Oligonucleotide

<400> SEQUENCE: 42
gatcccggtc tgggagcag cttctcca                                              28

<210> SEQ ID NO 43
<211> LENGTH: 28
<212> TYPE: DNA
<213> ORGANISM: Artificial Sequence
<220> FEATURE:
<223> OTHER INFORMATION: Oligonucleotide

<400> SEQUENCE: 43
gatccgccag agggagcag cttctcca                                              28

<210> SEQ ID NO 44
<211> LENGTH: 28
<212> TYPE: DNA
<213> ORGANISM: Artificial Sequence
<220> FEATURE:
<223> OTHER INFORMATION: Oligonucleotide

<400> SEQUENCE: 44
gatccgcctc tcccgagcag cttctcca                                             28

<210> SEQ ID NO 45
<211> LENGTH: 28
<212> TYPE: DNA
<213> ORGANISM: Artificial Sequence
<220> FEATURE:
<223> OTHER INFORMATION: Oligonucleotide

<400> SEQUENCE: 45
gatccgcctc tgggctccag cttctcca                                             28

<210> SEQ ID NO 46
<211> LENGTH: 28
<212> TYPE: DNA
<213> ORGANISM: Artificial Sequence
<220> FEATURE:
<223> OTHER INFORMATION: Oligonucleotide

<400> SEQUENCE: 46
gatccgcctc tgggaggtc cttctcca                                              28

<210> SEQ ID NO 47
<211> LENGTH: 28
<212> TYPE: DNA
<213> ORGANISM: Artificial Sequence
<220> FEATURE:
<223> OTHER INFORMATION: Oligonucleotide

<400> SEQUENCE: 47
gatccgcctc tgggagcag gaactcca                                              28

<210> SEQ ID NO 48
<211> LENGTH: 28

-continued

```
<212> TYPE: DNA
<213> ORGANISM: Artificial Sequence
<220> FEATURE:
<223> OTHER INFORMATION: Oligonucleotide

<400> SEQUENCE: 48
gatccgcctc tggggagcag cttgagga                                      28

<210> SEQ ID NO 49
<211> LENGTH: 389
<212> TYPE: DNA
<213> ORGANISM: Homo sapien
<220> FEATURE:

<400> SEQUENCE: 49
tcccattggc catcctcccc actctccaat tcggctccag aggcccctcc agactatagg    60
cagctgcccc tttaagcgtc gctactcctc ccccaagagc ggtggcaccg agggagttgg   120
ggtgggggga ggctgagcgc tctggctggg acagctagag aagatggccc aggctgggga   180
agtcgctctc atgccttgct gtcccctccc ctgagccagg tgatttggga gacccctcc    240 ttccttcttt ccctaccgcc ccacgcgcga cccggggatg gctccgtggc ctcacgagaa   300
cagctctctt gccccatggc cggacctccc caccctggcg cccaataccg ccaacacctg   360
ggctgccagg ggttccgtgg gaggcggca                                    389
```